(12) United States Patent
Parihar et al.

(10) Patent No.: US 7,288,075 B2
(45) Date of Patent: Oct. 30, 2007

(54) METHODS AND DEVICES UTILIZING RHEOLOGICAL MATERIALS

(75) Inventors: Shailendra K. Parihar, Monmouth Junction, NJ (US); Thomas P. Ryan, Flemington, NJ (US); Timothy Dietz, Califon, NJ (US); Parris S. Wellman, Hillsborough, NJ (US); Kevin S. Weadock, Princeton, NJ (US); T. Anh Le, Bridgewater, NJ (US); Peter Douglas, New Milford, NJ (US); Simon Cohn, North Arlington, NJ (US); Daniel Gordon, Newtown, PA (US); Rajesh Pendekanti, Bridgewater, NJ (US); Raghuveer Basude, Somerville, NJ (US); Robert S. Casar, Basking Ridge, NJ (US); Howard A. Stone, Cambridge, MA (US)

(73) Assignee: Ethicon, Inc., Somerville, NJ (US)

( * ) Notice: Subject to any disclaimer, the term of this patent is extended or adjusted under 35 U.S.C. 154(b) by 482 days.

(21) Appl. No.: 10/183,072

(22) Filed: Jun. 27, 2002

(65) Prior Publication Data

US 2004/0002665 A1    Jan. 1, 2004

(51) Int. Cl.
*A61B 5/103* (2006.01)
*A61B 5/117* (2006.01)
*A61B 5/00* (2006.01)
*A61C 19/00* (2006.01)
*A61C 9/00* (2006.01)
*A61C 5/04* (2006.01)
*A61C 19/04* (2006.01)

(52) U.S. Cl. ............ 600/590; 600/587; 600/589; 600/592; 600/300; 433/34; 433/37; 433/39; 433/41; 433/48; 433/68; 433/71

(58) Field of Classification Search ............... 600/300, 600/587, 589, 590, 592; 401/6; 606/1; 16/110.1, 16/421, 430; 381/312, 328; 36/25 R, 43, 36/71; 433/6, 34, 37, 39, 41, 48, 68, 71

See application file for complete search history.

(56) References Cited

U.S. PATENT DOCUMENTS

| 4,785,495 A | | 11/1988 | Dellis |
| 5,578,260 A | * | 11/1996 | DeSena ..................... 264/223 |
| 5,693,004 A | * | 12/1997 | Carlson et al. ............... 601/23 |
| 5,970,581 A | * | 10/1999 | Chadwick et al. ............ 16/421 |

(Continued)

OTHER PUBLICATIONS

Carlson, J. D., "What Makes a Good MR Fluid", 8th International Conference On Electrorheological (ER) Fluids and Magneto-rheological (MR) Suspensions, Nice Jul. 9-13, 2001.

Henrie, et al., "Variable Compliance Via Magneto-Rheological Materials", Proceedings of the 43rd International Symposium, Anaheim, CA, pp. 431-443, Jun. 1998.

(Continued)

*Primary Examiner*—Max F. Hindenburg
*Assistant Examiner*—Jeffrey G. Hoekstra

(57) ABSTRACT

Impression devices are provided for making an impression of a desired feature. The impression devices include: a flexible bladder having a cavity formed therein, the flexible bladder being capable of conforming to the details of the desired feature; a rheological material, such as a magnetorheological fluid, disposed in the cavity of the flexible bladder; and an activator for applying an external stimulus to the rheological material to change the state of the rheological material and thereby capture an impression of the desired feature.

2 Claims, 33 Drawing Sheets

U.S. PATENT DOCUMENTS

| | | | |
|---|---|---|---|
| 6,158,910 A * | 12/2000 | Jolly et al. | 401/6 |
| 6,179,797 B1 | 1/2001 | Brotz | |
| 6,251,065 B1 | 6/2001 | Kochamba et al. | |
| 6,473,512 B1 | 10/2002 | Junau | |
| 2003/0120353 A1 | 6/2003 | Christensen | |

OTHER PUBLICATIONS

Nakano, et al., "Electro-Rheological Fluids, Magneto-Rheological Suspensions and Their Applications", Proceedings for the 6th International Conference, Yonezawa, Japan, Jul. 22-25, 1997.

PCT Search Report dated Oct. 8, 2003, for PCT Application No. PCT/US03/18096.

* cited by examiner

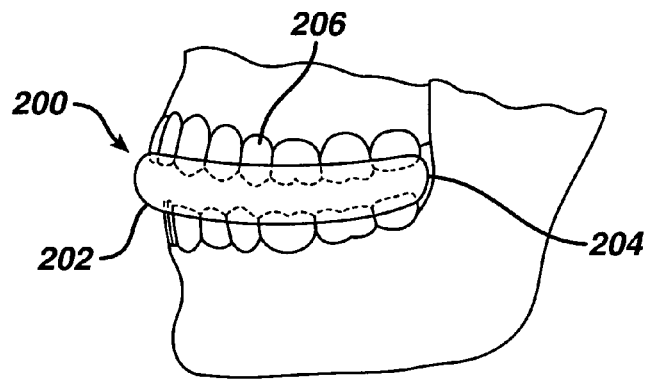
FIG. 2a
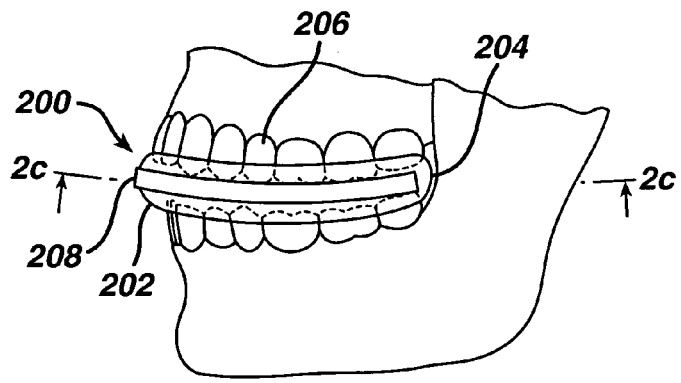
FIG. 2b
FIG. 2c
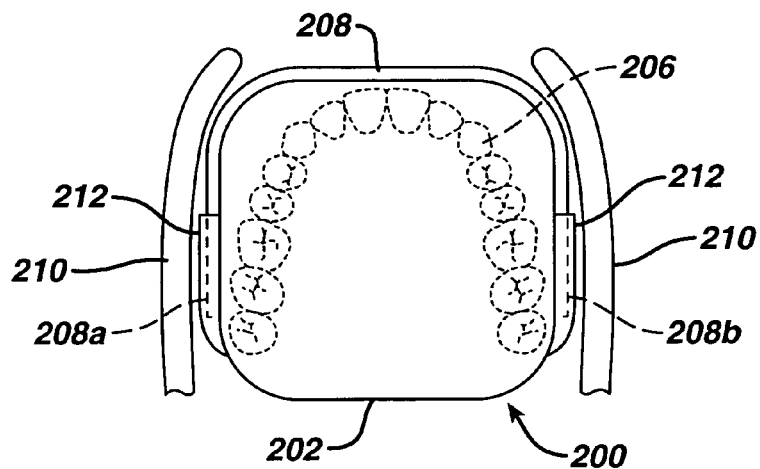

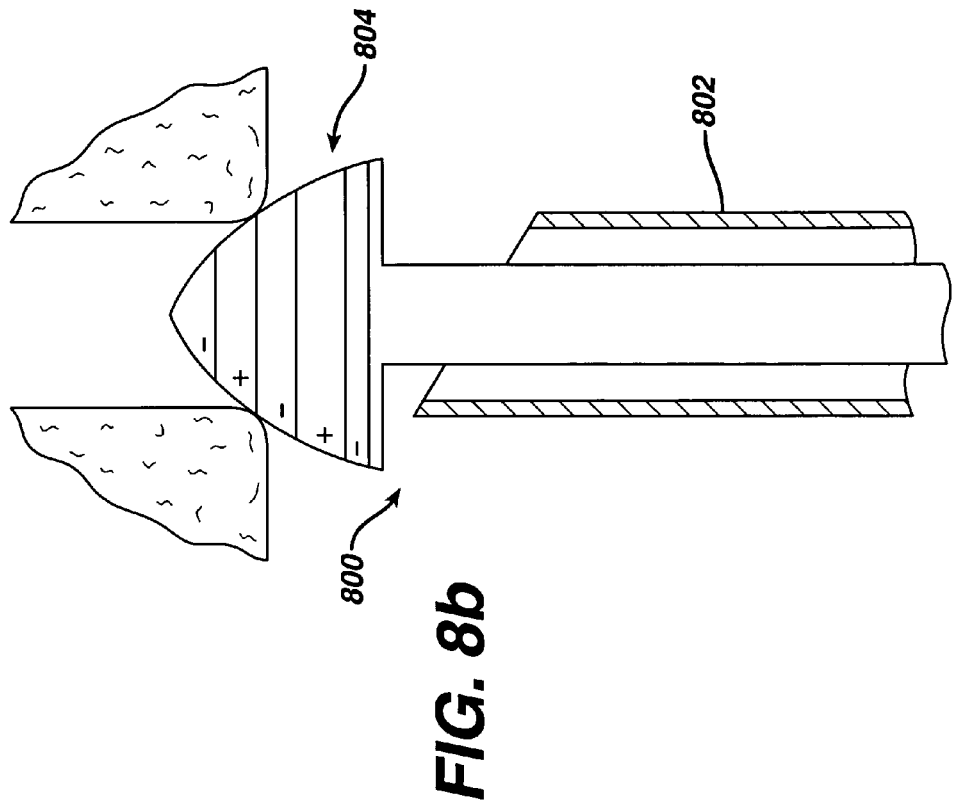
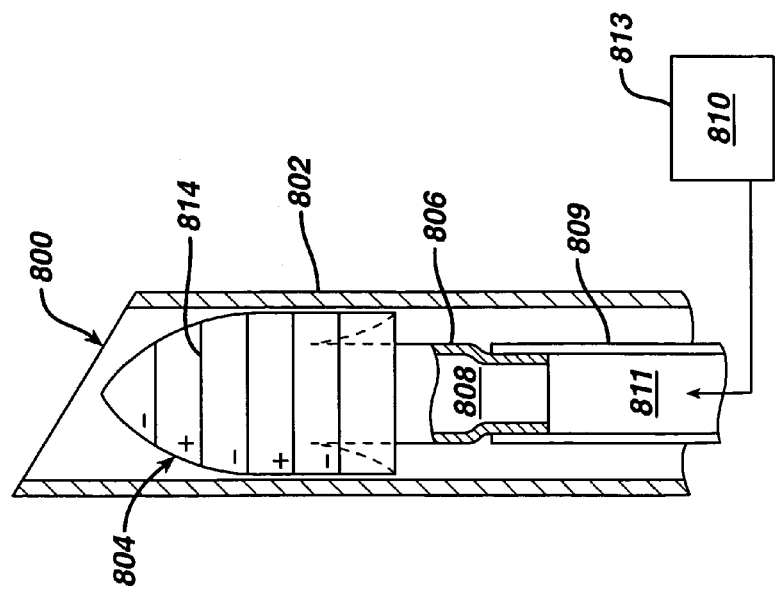

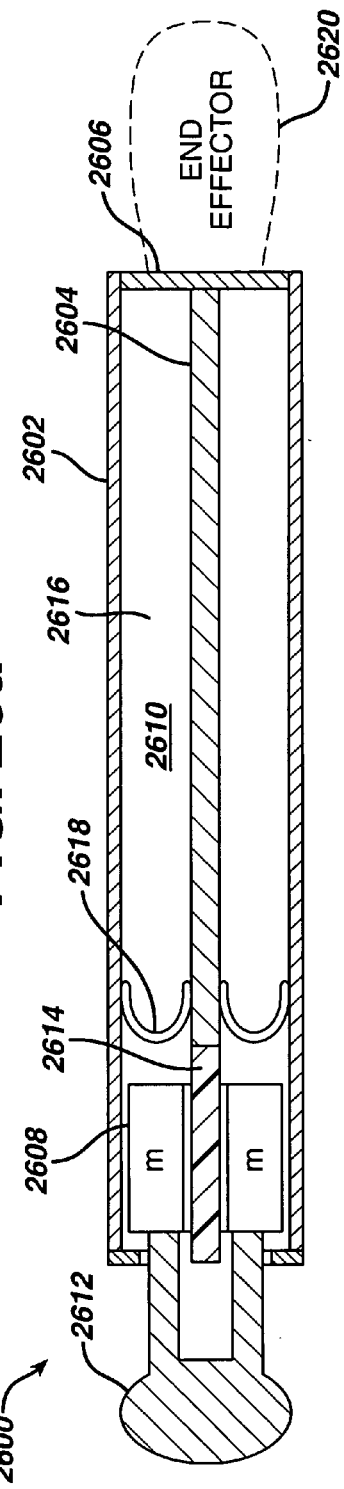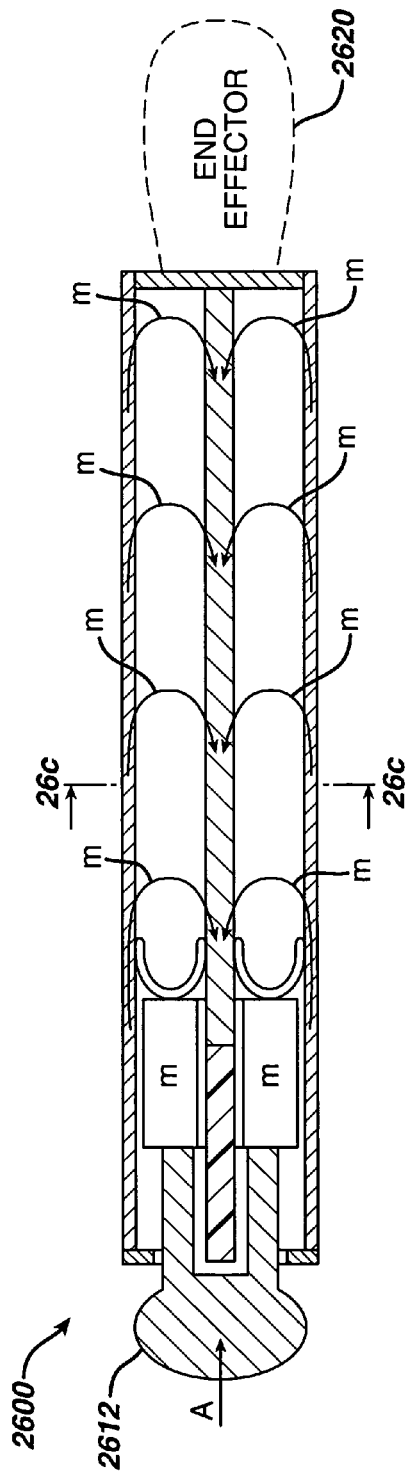

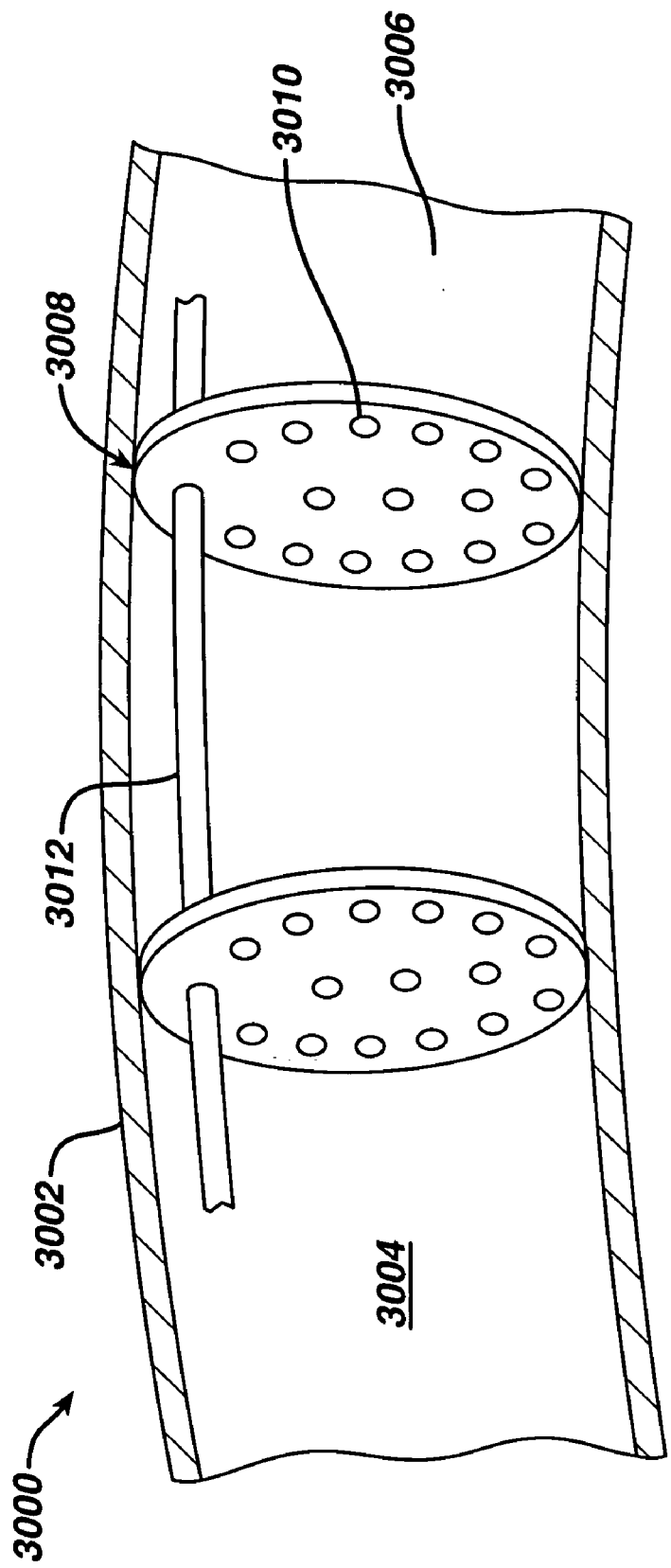

METHODS AND DEVICES UTILIZING RHEOLOGICAL MATERIALS

BACKGROUND OF THE INVENTION

1. Field of the Invention

The present invention relates generally to rheological materials, and more particularly, to methods and devices that utilize rheological materials, particularly, medical methods and devices.

2. Prior Art

Rheological materials refer to materials that change their state from a freely flowing liquid state to a stiffened near-solid state in response to an external stimulus. There are three basic types of rheological materials, they are electro-rheological (ER) fluids which change state in response to an applied electrical field, magneto-rheological (MR) fluids (also referred to as an MR suspension) which change state in response to an applied magnetic field, and liquid evacuation materials which change state in response to the evacuation of liquid from the material. The latter two rheological materials are referred to herein as rheological fluids.

Electro-rheological (ER) fluids are suspensions consisting of dielectric particles of size 0.1-100 m and dielectric base fluid. Since the dielectric constant of the suspension's particles differs from the dielectric constant of the base fluid, external electric field polarizes the particles. These polarized particles interact and form chain-like or even lattice-like organized structures. Simultaneously the rheological properties of the suspension change effectively, e.g. the effective viscosity increases dramatically.

ER fluids react rapidly to the applied field. The response time of electro-rheological fluids is of the order of 1-10 ms, which in principle enables the use of these liquids in such applications as electrically controlled clutches, valves and active damping devices.

ER suspensions also have a magnetic analog consisting of ferromagnetic particles and a base liquid. As the viscosity of the electro-rheological liquid can be controlled with the electric field strength, the viscosity of magneto-rheological (MR) fluid is sensitive to a magnetic field.

MR fluids are suspensions of micron-sized, magnetizable particles in a carrier fluid. Normally, MR fluids are free-flowing liquids having a consistency similar to that of motor oil. However, when a magnetic field is applied, their rheology changes, virtually instantly, to a near-solid consistency. Altering the strength of an applied magnetic field will precisely and proportionally control the consistency or yield strength of MR fluids, which behave as Bingham solids when in the presence of a magnetic field.

As shown in FIGS. 1a, 1b, and 1c, ER and MR fluids can be used in valve mode (FIG. 1a) with fluid flowing through an orifice, in a shear mode (FIG. 1B) with the fluid flowing between two surfaces which move relative to each other, or in squeeze film mode (FIG. 1c) where the fluid is compressed between two surfaces. In the absence of a magnetic field applied across a gap in which the fluid occupies, the fluid flows freely or allows free movement. In FIGS. 1a, 1b, and 1c, H denotes the applied magnetic field, F denotes the applied force, f denotes the fluid flow, and d denotes the displacement. Furthermore, reference numerals 100 and 102 denote first and second plates, respectively, while reference numeral 104 denotes a MR fluid disposed between the plates 100, 102. Examples of devices that utilize the valve mode include servo-valves, dampers, and shock absorbers. Examples of devices that utilize shear mode include clutches, brakes, and chucking and locking devices. Squeeze mode is typically utilized in applications having high forces and low motion. Although, FIGS. 1a, 1b, and 1c, are shown with regard to MR fluids, the modes illustrated therein are equally applicable to other rheological materials.

Upon application of a magnetic field, the particles align like chains with the direction of the field. The formation of these particle chains restricts the movement of the fluid within the gap since the fluid's yield strength is increased. Altering the inter-particle attraction by increasing or decreasing the strength of the field permits continuous control of the fluid's rheological properties and hence the damping or clutch or braking force.

Magneto-rheological or MR fluids are essentially suspensions of micron-sized, magnetizable particles in oil. Under normal conditions, a rheological fluid is a free-flowing liquid with a consistency similar to that of motor oil. Exposure to a magnetic field, however, can transform the fluid into a near-solid in milliseconds. Just as quickly, the fluid can be returned to its liquid state with the removal of the field. The degree of change in an MR fluid is proportional to the magnitude of the applied magnetic field. When subjected to the field, rheological fluids actually develop a yield strength and behave as Bingham solids. The change can appear as a very large change in effective viscosity. Iron particles in rheological MR fluids instantly form a chain when exposed to a magnetic field, changing the fluid from free-flowing to near solid.

MR fluids are similar to ER fluids but are 20-50 times stronger. They can also be operated directly from low-voltage power supplies and are far less sensitive to contaminants and extremes in temperature. Applied to a variety of devices, MR fluids can provide flexible control capabilities in designs that are far less complicated and more reliable than conventional electro-mechanical products.

Fluid evacuation materials are generally disposed in a flexible bladder that is connected to an evacuation means, such as a vacuum pump by one or more vacuum ports. The flexible bladder is substantially flexible when suction is not applied to the ports and is substantially rigid when vacuum is applied to the ports. The flexible bladder has beads suspended in a fluid, when suction is applied, the volume in the flexible bladder is collapsed, thereby urging the beads into a closer relationship and increasing the density thereof. The beads can take any shape, and can be shaped similarly or dissimilarly. In this state, the collapsed flexible bladder is substantially inflexible, resists bending, and retains a stiffened position. The flexible bladder can include a mesh and/or a plurality of cells to amplify the stiffening effect of the evacuation.

The following publications are recommended for a more thorough review of rheological materials and principles, Carlson, *What Makes a Good MR Fluid*, $8^{th}$ International Conference ON Electrorheological (ER) Fluids and Magneto-rheological (MR) Suspensions, Nice Jul. 9-13, 2001; Henrie et al., *Variable Compliance via Magneto-Rheological Materials*, Proceedings of the $43^{rd}$ International Symposium, Anaheim, Calif., pp. 431-443, Jun. 1998; and Nakano et al., *Electro-Rheological Fluids, Magneto-Rheological Suspensions and their Applications*, Proceedings for the $6^{th}$ International Conference, Yonezawa, Japan, Jul. 22-25, 1997, all of which are hereby incorporated by their reference.

SUMMARY OF THE INVENTION

Therefore it is an object of the present invention to provide methods and devices utilizing rheological materials.

Accordingly, an impression device for making an impression of a desired feature is provided. The impression device comprising: a flexible bladder having a cavity formed therein, the flexible bladder being capable of conforming to the details of the desired feature; and a rheological material disposed in the cavity of the flexible bladder.

Further provided is a method for making an impression of a desired feature. The method comprising: contacting a flexible bladder and the desired feature such that the flexible bladder conforms to the shape of the desired feature, the flexible bladder having a cavity formed therein and having a rheological material disposed in the cavity; and applying an external stimulus to the rheological material to change the state of the rheological material and thereby capture an impression of the desired feature.

Further provided is a surgical instrument comprising: a body; and an end-effector disposed on the body, the end-effector comprising: a flexible bladder defining a cavity; a rheological material disposed in at least a portion of the cavity; and activation means for applying an external stimulus to the rheological material to change the state of the rheological material.

Further provided is a method for performing a surgical procedure. The method comprising: inserting a surgical instrument having an end-effector to an intended site for performance of the surgical procedure, the end-effector having a flexible bladder defining a cavity, at least a portion of the cavity having a rheological material disposed therein; subsequent to or following the inserting, manipulating the end-effector into a desired shape; and activating the rheological material by application of an external stimulus to thereby change the state of the rheological material to a desired state.

Further provided is a surgical device comprising; a body; an end-effector disposed on the body, the end-effector having a flexible bladder defining a cavity; means for delivering a rheological material to the cavity to expand the flexible bladder; and activation means for activating the rheological material to a desired state.

Further provided is a method for performing a surgical procedure. The method comprising: inserting a surgical instrument having an end-effector to an intended site in a collapsed state for performance of the surgical procedure, the end-effector having a flexible bladder defining a cavity; expanding the end-effector into a desired shape by supplying a rheological material into the cavity; and activating the rheological material by application of an external stimulus to thereby change the state of the rheological material to a desired state.

Further provided is a trocar for use in a surgical procedure. The trocar comprising; a tubular body having a lumen for passage of a surgical instrument; a flexible bladder disposed in at least a portion of the lumen, the flexible bladder defining a cavity and having a rheological material disposed therein; and activation means for activating the rheological material to a desired state.

Further provided is a method for reducing the translation of unintended movement of a surgical instrument to an intended surgical site. The method comprising: providing a trocar having a tubular body defining a lumen for passage of the surgical instrument and a flexible bladder disposed in at least a portion of the lumen, the flexible bladder defining a cavity and having a rheological material disposed therein; disposing the surgical instrument in the trocar such that the flexible bladder is between a wall of the tubular body and the surgical instrument; and activating the rheological material to a desired state.

Still further provided is a support sac. The support sac comprising: a flexible bladder defining a cavity; a rheological material disposed in at least a portion of the cavity; and activation means for activating the rheological material to a desired state.

Still further provided is a method for supporting and/or lifting a bodily organ. The method comprising: placing a support sac under the organ to be lifted and/or supported, the support sac having a flexible bladder defining a cavity and a rheological material disposed in at least a portion of the cavity; manipulating at least a portion of the support sac to lift and/or support the organ; and activating the at least a portion of the support sac to a desired state.

Still further provided is a sphincter implant. The sphincter implant comprising: a doughnut shaped flexible bladder defining an annular cavity; a rheological material disposed in the annular cavity; and activation means for activating the rheological material to a desired state.

Still further provided is a method for artificially constricting an opening. The method comprising: placing a sphincter implant around the opening, the implant having a flexible bladder defining a cavity and a rheological material disposed in the cavity; activating the rheological material to a desired state to constrict the opening; and inactivating the rheological material to a relaxed state to release the constriction of the opening.

Still further provided is a penile implant comprising: a flexible bladder defining a cavity; a rheological material disposed in the cavity; activation means for activating the rheological material to a desired state; and delivery means for delivering the rheological material to the flexible bladder when an erection is desired.

Still further provided is a method for creating an erection in a person. The method comprising: placing a penile implant around the person's penis, the implant having a flexible bladder defining a cavity; delivering the rheological material to the cavity when an erection is desired; subsequent to the delivering, activating the rheological material to a desired state; and inactivating the rheological material and withdrawing the rheological material from the cavity when an erection is no longer desired.

Still further provided is a cast/splint for a body part. The cast/splint comprising: a flexible bladder disposed around the body part, the flexible bladder defining a cavity; a rheological fluid disposed in the cavity; and activation means for activating the rheological fluid to a desired state.

Still further provided is a method for setting a broken bone. The method comprising: disposing a flexible bladder around the broken bone, the flexible bladder defining a cavity having a rheological fluid disposed therein; and activating the rheological fluid to a desired state.

Still further provided is an atrial fibrillation restraining device. The device comprising: a flexible bladder disposed in the heart, the flexible bladder defining a cavity; a rheological material disposed in the cavity; means for detecting abnormal vibrations in the heart; and means for activating the rheological material in response to the detected abnormal vibrations.

Still further provided is a method for restraining atrial fibrillation of the heart. The method comprising: disposing a flexible bladder in the heart, the flexible bladder defining a cavity and having a rheological material disposed in the cavity; detecting abnormal vibrations in the heart; and activating the rheological material in response to the detected abnormal vibrations.

Still further provided is an organ/conduit restricting device. The device comprising: a flexible bladder positioned on the organ/conduit, the flexible bladder defining a cavity; a rheological material disposed in the cavity; and activation means for activating the rheological material to a desired state in response to a need to restrict the organ/conduit.

Still further provided is a method for restricting an organ/conduit. The method comprising: positioning a flexible bladder on the organ/conduit, the flexible bladder defining a cavity and having a rheological material disposed in the cavity; and activating the rheological material to a desired state in response to a need to restrict the organ/conduit.

Still further provided is a punch for punching a hole in a sheet material. The punch comprising: a piercing member having a tip for piercing the sheet material; a collapsible and expandable anvil disposed on the piercing member, the anvil comprising a flexible bladder defining a cavity; a punch member having a cutting edge for cutting the hole, the punch member being movably disposed relative to the anvil; delivery means for delivering a rheological material into the cavity; and activation means for activating the rheological material to a desired state Still further provided is a method for creating a hole in a sheet material. The method comprising: piercing the sheet material with a piercing member such that a collapsed anvil disposed on the piercing member passes through the sheet material, the anvil comprising a flexible bladder defining a cavity; expanding the anvil by delivering a rheological material to the cavity; activating the rheological material to a desired state; and moving a cutting edge relative to the anvil to cut the hole in the sheet material.

Still further provided is a first variation of a shaft for manipulation into a desired position and to be locked into the desired position. The shaft comprising: a base for connecting to at least a portion of a structure; a flexible bladder connected at a first end to the base, the flexible bladder defining a cavity; a rheological fluid disposed in the cavity; and activation means for activating the rheological material after manipulation of the flexible bladder into a desired position to thereby lock the flexible bladder into the desired position.

Still further provided is a second variation of a shaft for manipulation into a desired position and to be locked into the desired position. The shaft comprising: a base for connecting to at least a portion of a structure; at least two links connected together, one of the links being connected to the base, each of the at least two links being pivotably disposed with respect to each other and having at least one extensible piston, the at least one extensible piston having a compressible fluid disposed therein; a reservoir for holding the compressible fluid; tubing in fluid communication with each of the extensible pistons and the reservoir, the tubing supplying the compressible fluid to the extensible pistons which are extended during a manipulation of the at least two links and withdrawing the compressible fluid from the extensible pistons which are retracted during a manipulation of the at least two links; and a valve disposed in the tubing for restricting the flow of the compressible fluid to and from the extensible pistons after the shaft is manipulated into a desired position thereby locking the shaft in the desired position.

Still further provided is a method for locking a shaft into a desired position. The method comprising: manipulating the shaft into the desired position, the shaft comprising a flexible bladder which defines a cavity and has a rheological fluid disposed in the cavity; activating the rheological fluid into a desired state to thereby lock the shaft into the desired position.

Still further provided is a method for locking a shaft into a desired position. The method comprising: manipulating the shaft into the desired position, the shaft comprising at least two links connected together, each of the at least two links being pivotably disposed with respect to each other and having at least one extensible piston, the at least one extensible piston having a compressible fluid disposed therein; supplying the compressible fluid to the extensible pistons which are extended during a manipulation of the at least two links and withdrawing the compressible fluid from the extensible pistons which are retracted during a manipulation of the at least two links; and restricting the flow of the compressible fluid to and from the extensible pistons after the shaft is manipulated into a desired position thereby locking the shaft in the desired position.

Still further provided is a soft tissue retractor comprising: a flexible bladder defining a cavity; a rheological material disposed in the cavity; and activation means for activating the rheological material in a desired shape within an opening in tissue.

Still further provided is a method for retracting an incision in soft tissue for passage of an instrument therein. The method comprising: making the incision in the tissue; placing a soft tissue retractor in the incision, the soft tissue retractor having a flexible bladder which defines a cavity, the cavity having a rheological material disposed therein; manipulating the soft tissue retractor to an open position; and activating the rheological material to lock the soft tissue retractor in the open position.

Still further provided is an instrument comprising: an end-effector; a flexible bladder defining a cavity and a rheological material disposed in the cavity; means for activating the rheological material in the cavity; and means for restricting the movement of the end-effector upon the activation of the rheological material.

Still further provided is a method for restricting the movement of an end effector of an instrument. The method comprising: providing the instrument with a flexible bladder defining a cavity and a rheological material disposed in the cavity; activating the rheological material in the cavity; and restricting the movement of the end-effector upon the activation of the rheological material.

Still further provided is a device comprising: a rheological fluid disposed in a cavity; a vibrating member disposed in the cavity; and means for vibrating the vibrating member to agitate the rheological fluid.

Still further provided is a method for agitating a rheological fluid contained in a cavity. The method comprising: disposing a vibrating member in the cavity; and vibrating the vibrating member to agitate the rheological fluid.

Still further provided is a conformable shaft comprising: an outer shaft defining a lumen, the outer shaft having at least a portion thereof which has a high magnetic permeability; a rheological material disposed in at least a portion of the lumen; at least one activation magnet disposed in the lumen and slidable between a shielded position and an unshielded position; activation means for providing a magnetic field circuit to activate the MR fluid when the magnet is slid into the unshielded position; and inactivation means for opening the magnetic field circuit to inactivate the MR fluid when the magnet is slid into the shielded position.

Still yet further provided is a method for manipulating and stiffening a conformable shaft into the manipulated position. The method comprising: providing an outer shaft defining a lumen, the outer shaft having at least a portion thereof which has a high magnetic permeability; disposing a rheological material in at least a portion of the lumen; providing at least one activation magnet disposed in the lumen and slidable between a shielded position and an unshielded position; activating the MR fluid when the magnet is slid into the unshielded position to provide a magnetic field circuit; and opening the magnetic field circuit to inactivate the MR fluid when the magnet is slid into the shielded position.

BRIEF DESCRIPTION OF THE DRAWINGS

These and other features, aspects, and advantages of the apparatus and methods of the present invention will become better understood with regard to the following description, appended claims, and accompanying drawings where:

FIGS. 2a and 2b illustrate a bite bag for making dental impressions, FIG. 2a illustrating the bite bag in a fluid state and FIG. 2b illustrating the bite bag activated by placement of a magnet therein to solidify the bite bad into a near solid state.

FIG. 2c illustrates a sectional view of FIG. 2b as taken along line 2c-2c therein.

FIG. 3c illustrates a magnet for use in the conformable handle of FIG. 3a.

FIG. 8a illustrates an electrosurgical device in a collapsed state being passed through a trocar tube.

FIG. 8b illustrates the electrosurgical device of FIG. 8a after it has passed through the trocar and after it has been expanded.

FIG. 13b illustrates an alternative version of the cast/splint of FIG. 13a.

FIG. 19b illustrates the valve of the surgical stabilizer of FIG. 19a.

FIG. 24a illustrates a bladder having a rheological material withdrawn therefrom and FIG. 24b illustrates the bladder having the rheological material pumped therein.

FIG. 25a illustrates a bladder having a rheological material withdrawn therefrom and FIG. 25b illustrates the bladder having the rheological material pumped therein.

FIGS. 26a and 26b illustrate sectional views of a conformable shaft in an inactivated and activated configuration, respectively.

FIG. 27a illustrates a portion of a sectional view of an alternative configuration of the conformable shaft of FIG. 26a.

FIG. 27b illustrates a sectional view of the conformable shaft as taken along line 27b-27b of FIG. 27a.

FIG. 28a illustrates a portion of a sectional view of yet another alternative configuration of the conformable shaft of FIG. 26a.

FIGS. 28b and 28c illustrate sectional views of the conformable shaft as taken along line 28b-28b of FIG. 28a.

FIGS. 29b and 29c illustrate sectional views of the conformable shaft as taken along line 29b-29b in FIG. 29a.

FIG. 30 illustrates yet another embodiment of a conformable shaft.

FIG. 31b illustrates a sectional view of a shaft segment of the conformable shaft of FIG. 31a.

DETAILED DESCRIPTION OF THE PREFERRED EMBODIMENT

Figure 1A:
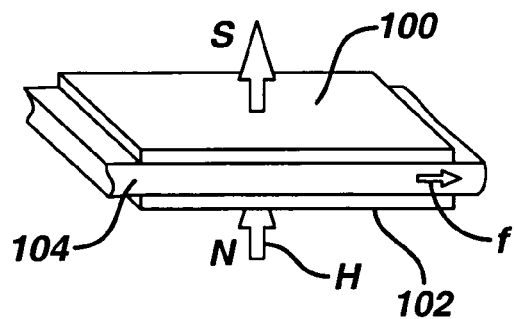
FIGS. 1a, 1b, and 1c illustrate three general modes in which devices utilizing rheological fluids operate, valve mode, shear mode, and squeeze mode, respectively.
Figure 1B:
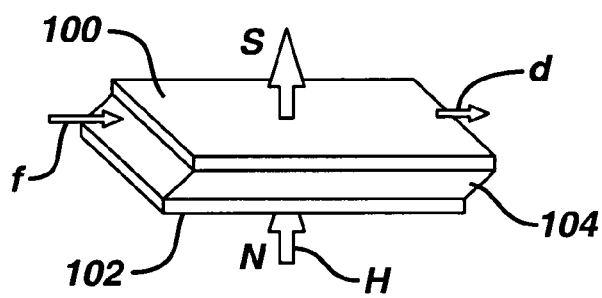
Figure 1C:
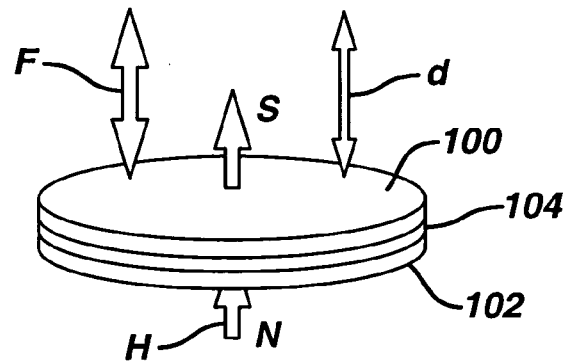

Although this invention is applicable to numerous and various types of methods and devices, it has been found particularly useful in the environment of medical methods and devices. Therefore, without limiting the applicability of the invention to medical methods and devices, the invention will be described in such environment.

Furthermore, although the devices and methods discussed below may be described with regard to less than all three types of rheological materials outlined above (ER, MR, and fluid evacuation), they are described as such by way of example only and not to limit the scope or spirit of the present invention. Notwithstanding the description thereof, it will be understood to those skilled in the art that the methods and devices of the present invention are equally applicable to all three types of rheological materials discussed above, specifically, they are applicable to ER, MR, and fluid evacuation rheological materials unless otherwise described.

Additionally, in the following disclosure, the word "activated" and forms thereof are used to describe the application of an external stimulus to the rheological materials that cause their change of state from a liquid to a near solid, or any state therebetween. For example, placing a magnet in proximity to an MR fluid is described herein as activating the MR fluid. In this example, activation means to change the MR fluid's state from a liquid to a desired state, such as a near solid.

Referring now to FIGS. 2a and 2b, there is illustrated a bite bag 200 for use in dentistry. The mouth 204 of FIGS. 2a and 2b are shown without the overlying skin, such as the cheeks, for clarity. Specifically, the bite bag 200 is used to make dental impressions of teeth for various reasons, such as to make a mold for fabricating teeth or for providing and cataloging dental records. The bite bag 200 comprises a flexible bladder 202 that is filled, at least partially, with an MR fluid (not shown). The flexible bladder 202 is preferably a thin elastomer bag capable of conforming to the smallest detail of human teeth and which is medically acceptable for use in the mouth. A preferred material is medical grade silicone.

In use, the bite bag 200 is placed in a person's mouth 204, as is shown in FIG. 2a. The person bites down on the bite bag 200 to make an impression in the flexible bladder, such that the flexible bladder and MR fluid therein, conform to the details of the persons teeth 206. The bite bag 200 may be submerged in warm water to increase the pliability of the flexible bladder 202 prior to insertion of the bite bag 200 in the mouth. Other means may also be used to increase the pliability of the flexible bladder 202.

After the flexible bladder 202 has been given sufficient time to conform to the details of the persons teeth, a magnet 208 is placed in proximity to the bite bag 200 to activate the MR fluid to change its state, preferably, to a near solid, thereby "freezing" the impression of the persons teeth 206 in the flexible bladder 202.

Referring now to FIGS. 2b and 2c, preferably, the magnet 208 is U-shaped and fits between the teeth 206 and cheeks 210 on both sides of the person's mouth 204. In this configuration, the magnet 208, and thus, the magnetic field generated therefrom, are closest to the area to be activated, namely, the person's teeth 206. More preferably, the flexible bladder 202 has pockets 212 formed thereon for acceptance of first and second ends 208a, 208b of the u-shaped magnet 208. The bite bag 200 and magnet 208 are then removed from the patient's mouth 204. After removal, the pockets 212 help retain the magnet 208 in place such that the MR fluid does not return to its liquid state. While the magnet 208 is shown as a single piece unit, it may consist of two or more elements to facilitate introduction into the person's mouth and positioning in the pockets 212. Those skilled in the art will realize that the u-shaped magnet 208 is given by way of example only and not to limit the scope or spirit of the bite bag of the present invention. Many magnet configurations are possible, such as a disc or cylindrical shaped magnet (not shown) that is disposed in an interior cavity formed in the bite bag. Furthermore, those skilled in the art will also realize that although MR fluids are preferred, ER fluids or fluid evacuation materials can also be used with the bite bag. Lastly, the bite bag is given by way example only and not to limit the scope or spirit of the present invention, those skilled in the art will realize that the bag filled with a rheological material has general applications other than dentistry, for example in replicating other items from an impression, such as archeological objects, jewelry, and architectural features.

Figure 3A:
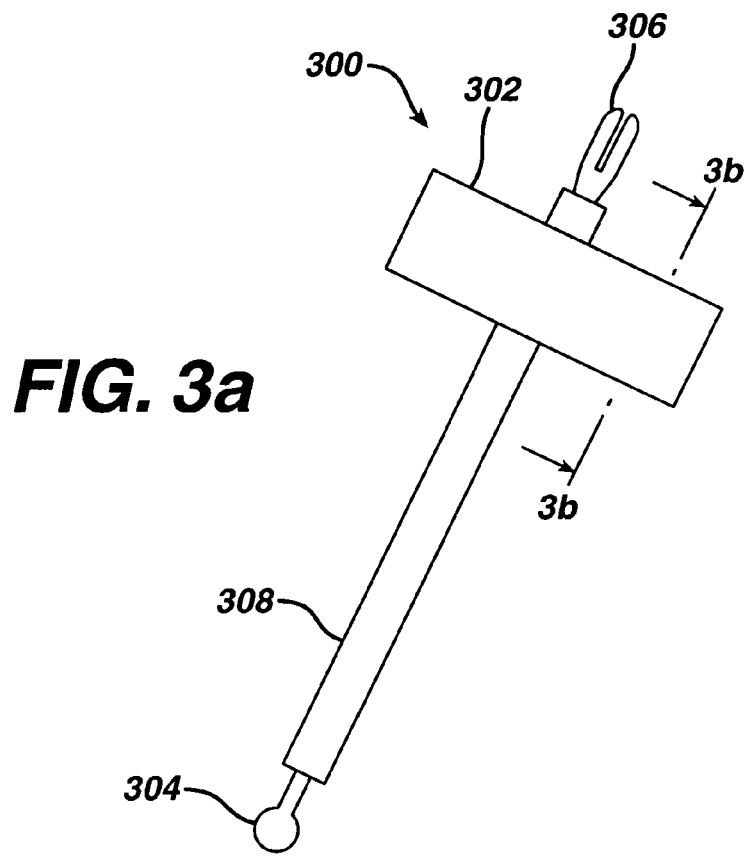
FIG. 3a illustrates an electrosurgical instrument having a T-style conformable handle.
Figure 3B:
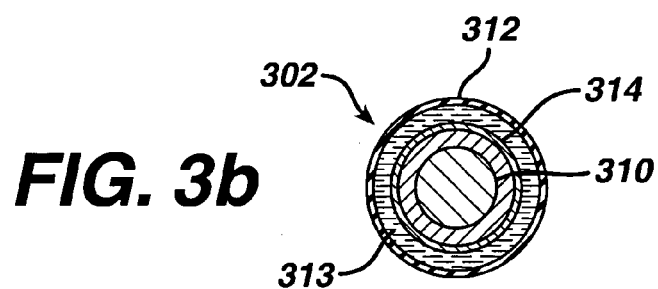
FIG. 3b illustrates a sectional view of the conformable handle of FIG. 3a as taken along line 3b-3b therein.
Figure 3C:
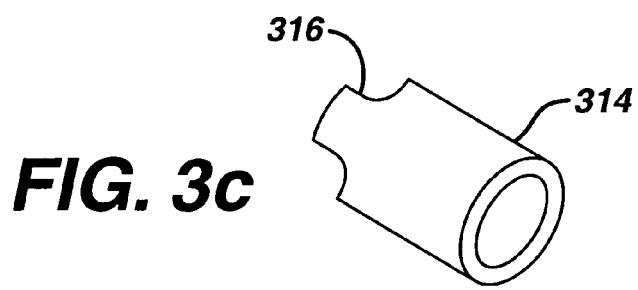

Referring now to FIGS. 3a, 3b, and 3c, there is illustrated a surgical instrument 300 having a conformable handle 302. The surgical instrument shown is an electro-cautery device having an electro-cautery end-effector 304 that is energized with radio-frequency (RF) energy through connector 306 for cauterizing tissue. Those skilled in the art will appreciate that the electro-cautery surgical instrument is given by way of example only and not to limit the scope or spirit of the present invention. Not only can other medical instruments utilize the conformable handle 302 of the present invention, but non-medical instruments, such as a hammer, can also benefit from the conformable handle 302 described below.

The electrosurgical instrument 300 has a slender tubular body 308 having the end-effector 304 at a distal end and the electrocautery connector 306 at a proximal end. The conformable handle 302 is configured as a T-style handle that crosses the tubular body 308 orthogonally. The conformable handle 302 preferably has a rigid core member 310 that is rigidly connected to the tubular body 308 at a predetermined place along the length of the tubular body 308. A cylindrical flexible bladder 312 is disposed over the rigid core member 310. Preferably, the flexible bladder 312 is a sheet that is wrapped around the rigid core member 310 and sealed along a seam to form its cylindrical shape. The sheet further has holes corresponding to where the tubular body 308 intersects the rigid core member 310. The flexible bladder holds a rheological material 313, preferably an MR fluid. As discussed above with regard to the bite bag, the flexible bladder is preferably fabricated from a thin elastomer, such as silicone.

Preferably, an annular gap exists between the rigid core member 310 and the flexible bladder 312 for insertion of a cylindrical activation magnet 314. The cylindrical activation magnet 314 is preferably formed in two pieces and inserted from each end of the conformable handle 302, one such piece is illustrated in FIG. 3c. Although the rigid core member 310 is preferred, it is not essential. For instance, the cylindrical flexible bladder may only have a cylindrical hole formed at its center for insertion of a cylindrical magnet therein.

In operation, a user grasps the conformable handle 302 to make an impression of his or her hand in the flexible bladder 312. While grasping the handle, the magnets 314 are inserted into the annular gap between the flexible bladder 312 and rigid core member 310 from each end of the handle 302. Preferably, the magnets 314 are rotated 90 degrees such that tabs 316 provided on the magnets 314 envelop the portion of the conformable handle 302 that overlaps with the tubular body 308. After insertion of the magnets 314, the MR fluid is activated to change its state to that desired depending upon the strength of the generated magnetic field. In some applications a near solid may be desired while others may require a softer handle such as that having the consistency of a gel.

The T-style handle discussed with regard to FIG. 3a is given by way of example only and not to limit the scope or spirit of the present invention. Other examples of conformable handle styles are possible including the pistol grip style conformable handle illustrated in FIG. 4a and the in-line style conformable handle illustrated in FIG. 4b. The pistol grip handle 400 of FIG. 4a has first and second grips 402, 404, either or both of which can be conformable to the operator's hand shape and size. The in-line style conformable handle 450 illustrated in FIG. 4b is conceptually similar to that of FIG. 3a. Preferably, similarly to that described with regard to FIGS. 3a and 3b, the pistol grip and in-line style conformable handles 400, 450 utilize a flexible bladder having an MR fluid therein, a rigid core member and a means for inserting an activating magnet therein.

Figure 4A:
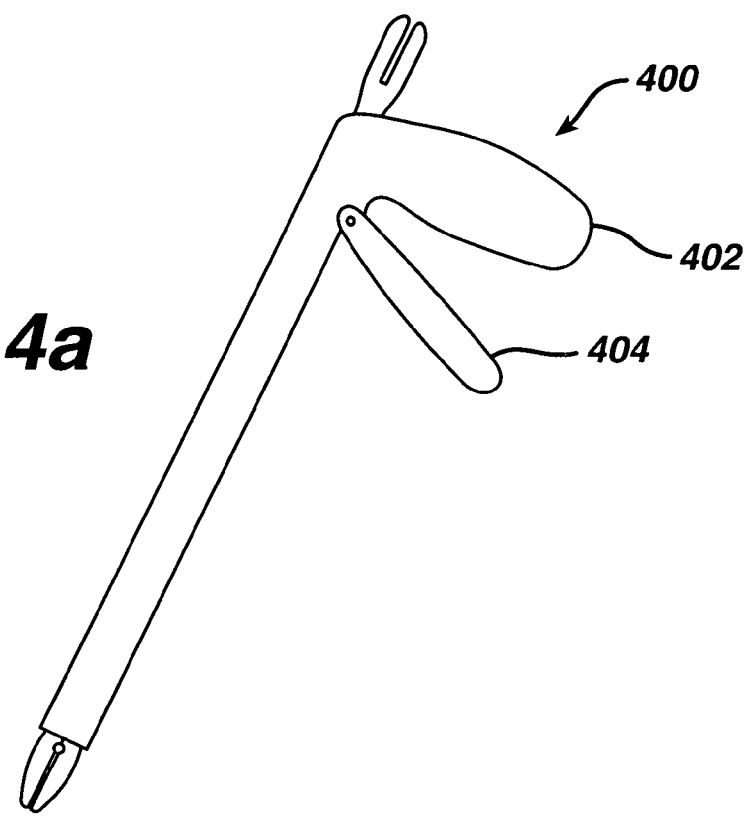
FIGS. 4a and 4b illustrates variations of electrosurgical instruments having pistol grip and in-line handles, respectively.
Figure 4B:
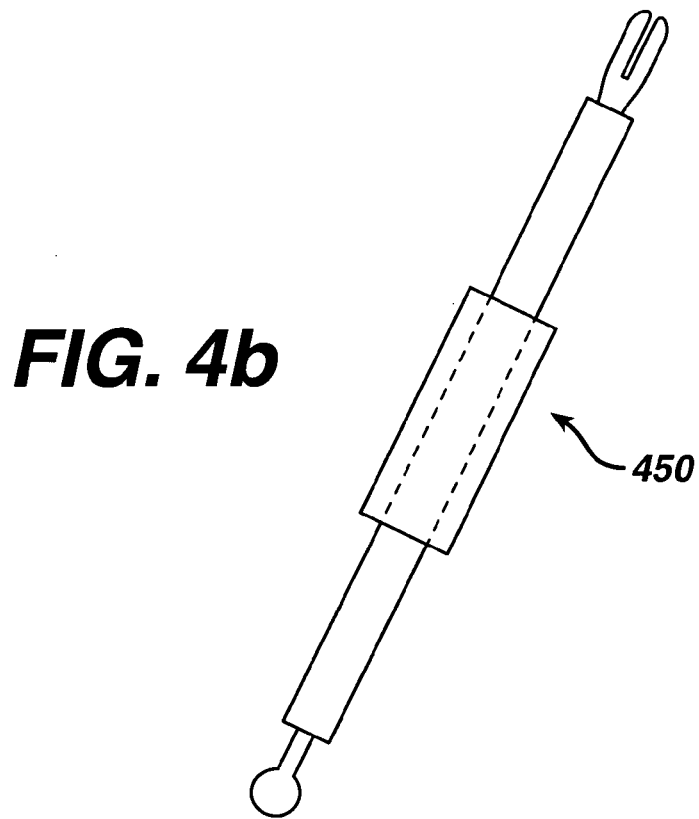

Although the conformable handles 302, 400, 450 of FIGS. 3a, 4a, and 4b are described with regard to MR fluids and a magnet for activation thereof, other types of rheological materials and/or means for activation are possible. For example, the MR fluid can be activated by generating a magnetic field with electrically conductive coils (not shown) through which current is supplied. Furthermore, ER fluids and fluid evacuation materials may also be utilized in the conformable handles 302, 400, 450.

Figure 5:
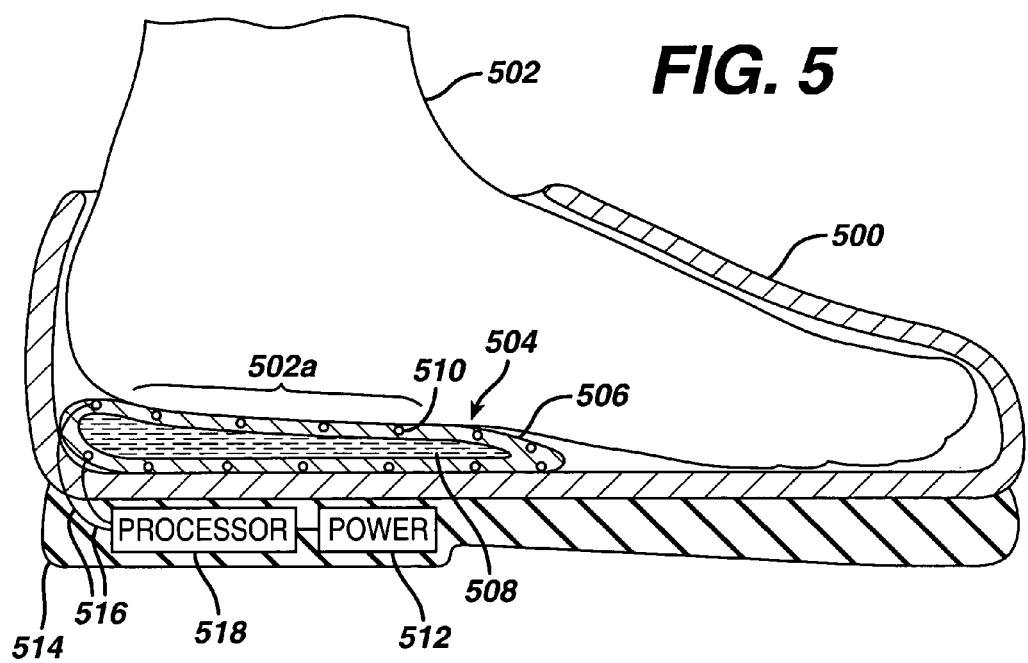
FIG. 5 illustrates a sectional view of a shoe insert having a rheological material therein, the shoe insert being disposed in a heel portion of a shoe.

Referring now to FIG. 5, there is illustrated a shoe 500 having a human foot 502 therein. The shoe 500 includes a shoe insert 504 disposed in a heel portion corresponding to the heel 502a of the foot 502. Although, shown with regard to the heel portion 502a, the shoe insert 504 can correspond to another portion of the foot, such as the arch, more than one section of the foot 502 such as the heel and the arch, or the entire sole of the foot 502. The insert 504 includes a flexible bladder 506 having a cavity with rheological material 508 disposed therein. The rheological material is preferably a MR fluid. As discussed above with regard to the bite bag and conformable handle, the flexible bladder is preferably fabricated from a thin elastomer, such as silicone.

Preferably, like the bite bag and conformable handle, the insert 504 is activated by the application of a magnetic field. However, unlike the bite bag and conformable handle in which the magnetic field is preferably generated by a magnet, the magnetic field for the insert 504 is preferably generated by an electromagnet comprising coils of conductors 510. A magnetic field is generated from passing current through the conductors 510 as is well known in the art. The conductors 510 are preferably integrally formed with the flexible bladder 506 walls or adhered thereto. Power is preferably supplied to the conductors 510 from a power supply 512, such as a battery, which is preferably embedded in the heel 514 of the shoe 500. A switch (not shown) is used to selectively turn on and of the supply of power to the conductors 510 via leads 516.

The magnetic field generated by the conductors 510 activates the MR fluid 508 to change its state from a liquid to a desired degree of solidness depending upon the strength of the generated magnetic field. For example, the insert 504 can become a near solid for support of the arch or a gel for damping of forces on the heel due to running. Furthermore, a processor 518 may be utilized for turning the power supply on and off for predetermined lengths of time and at predetermined intervals. This has the effect of massaging the foot by periodically activating and unactivating the MR fluid 508 in the insert 504.

Figure 6A:
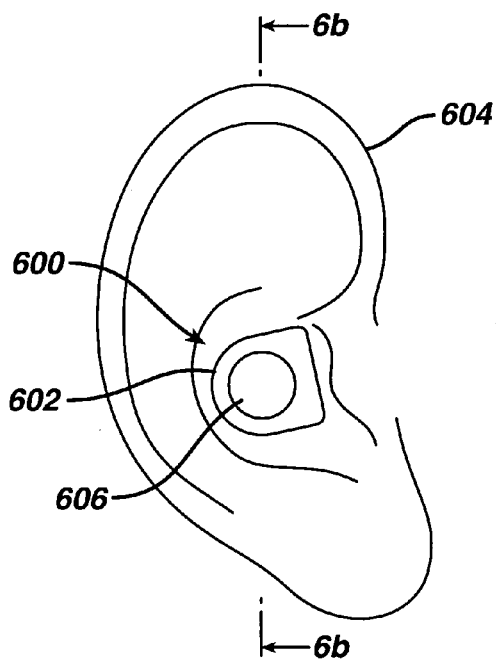
FIG. 6a illustrates a human ear having a conformable ear plug/hearing aid disposed therein.
Figure 6B:
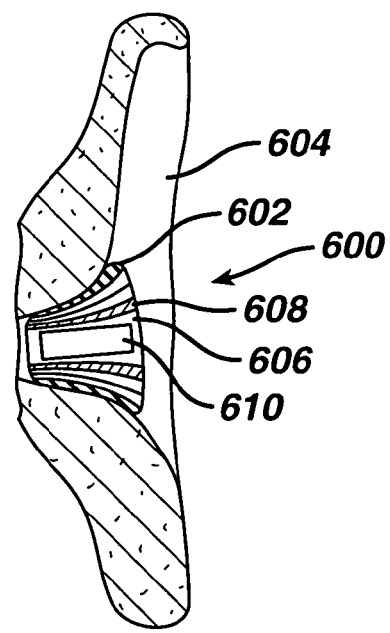
FIG. 6b illustrates a sectional view of the human ear of FIG. 6a as taken along line 6b-6b therein.

Referring now to FIGS. 6a and 6b, there is illustrated a conformable earplug/hearing aid 600, which can be configured in either an earplug or hearing aid configuration. However, for purposes of this disclosure, the same will be referred to as a hearing aid. Although the hearing aid 600 is described with regard to an in-the-ear (ITE) type, those skilled in the art will realize that other types are also applicable, such as a completely-in-the-canal (CIC) hearing aid, an in-the-canal (ITC) hearing aid, or a behind-the-ear (BTE) hearing aid. The hearing aid includes a flexible bladder 602 which has a cavity at least partially filled with a rheological material, preferably, a MR fluid. The flexible bladder 602 is shaped and sized to be inserted in the appropriate portion of the ear 604 depending on the type of hearing aid used. The flexible bladder 602 is preferably in the shape of a tapered cylinder that defines a hole. After insertion of the flexible bladder 602 into the ear 604, the MR fluid is activated by inserting a plug 606 in the hole, thereby conforming the flexible bladder to the shape of the ear 604. The plug 606 contains a magnet 608 and the electronics 610 of the hearing aid therein. In the earplug configuration, the flexible bladder 602 is substantially similar to that of the hearing aid and the plug 606 differs in that it does not contain the electronics 610. A shield (not shown) may also be provided to isolate the electronics 610 from the magnet 608.

Figure 6C:
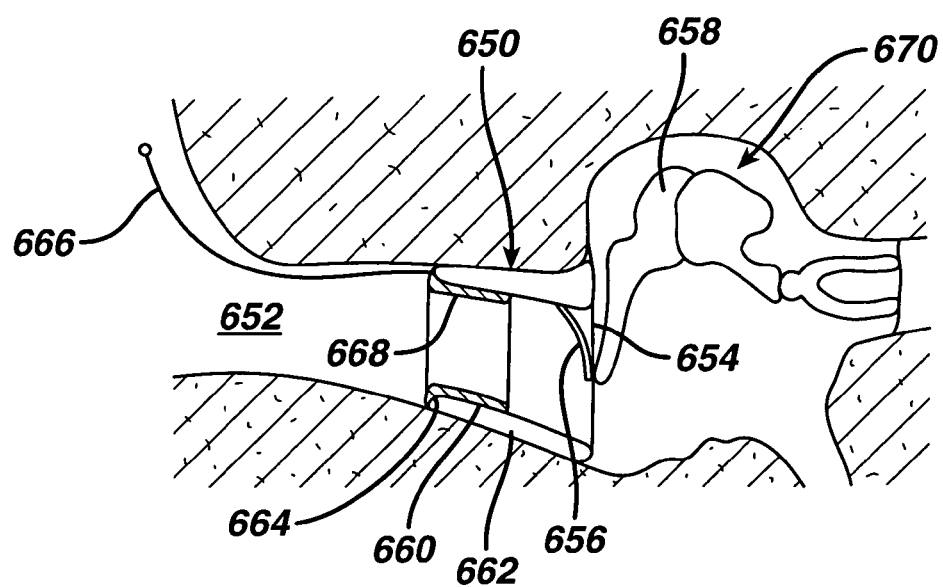
FIG. 6c illustrates a sectional view of an ear canal having a conformable ear collar positioned therein.

Referring now to FIG. 6c there is shown an alternative embodiment of a hearing aid. FIG. 6c illustrates a conformable ear collar, generally referred to by reference numeral 650. The ear collar 650 is disposed in the ear canal 652 proximate the tympanic membrane 654. The ear collar 650 further has an actuator 656 for directly actuating the malleus 658 through the tympanic membrane 654.

The ear collar 650 comprises a flexible bladder 660 defining a cavity 662 in which a rheological material, preferably an MR fluid 664 is disposed. The actuator 656 is fixed to the collar 650 and is preferably a piezoelectric device, a permanent magnet, or an electrostatic device. An electrical lead 666 is used to power the actuator 656 and provide a control signal to transmit audible frequencies to the actuator 656. The lead 666 preferably contains two or three insulated wires, at least one of which may also be used to activate the rheological material 664 in the cavity 662 of the flexible bladder 660. Alternatively, the actuator 656 can be controlled and powered by a wireless RF signal which is relayed to the actuator 656 by a receiver coil (not shown) disposed in the cavity 662. It should be noted that if a magnet is used to activate the MR fluid, the electronic circuitry for the RF control signal is designed such that the magnetic field from the magnet does not interfere with the RF control signal.

In operation, the ear collar 650 is placed in the ear canal 652 near the tympanic membrane 654. The flexible bladder 660 is then conformed to the shape of the ear canal 652. This can be accomplished in a number of ways. For example, additional MR fluid can be delivered to the cavity 662 by way of a syringe (not shown) or other delivery means. Preferably, a tool (not shown) is placed in the ear canal 652, the tool having an end portion, which can have a leading taper, which urges the portions of the ear collar 650 radially outward against the walls of the ear canal 652.

Subsequent to conforming the flexible bladder 660 to the shape of the ear canal 652, the MR fluid, or other rheological material 664 is activated, preferably by placing a magnet 668 in proximity to the flexible bladder 660. The magnet 668 can also be used to conform the flexible bladder 660 to the shape of the ear canal 652 by urging the bladder 660 radially outward and can be deployed from the tool (not shown) previously discussed. Other rheological materials can be used along with other types of activation, such as ER fluids which are activated by an electrical current or MR fluids which are activated by an electromagnet, preferably carried in or on the flexible bladder 660.

Once the MR fluid 664 is activated, the actuator 656 has a rigid platform to work against. The actuator 656 under the control of a controller (not shown) pushes on the malleus 658 to vibrate the same which in turn causes the remainder of the ossicular chain 670 to vibrate, thereby at least partially restoring a hearing loss. Those skilled in the art will appreciate that the ear collar 650 helps in aiding or restoring a hearing loss without the disadvantages of a traditional hearing aid which completely blocks the ear canal 652. Such disadvantages include muffling and distortion of the sound to the ear. The ear collar 650 is removed by removing the magnet 668 (or other activation source) and removing the ear collar 650.

In an alternative embodiment, the ear collar 650 is used to provide negative mechanical feedback from the ossicular chain 670 linkage to the tympanic membrane 654 (i.e., the contact point with the malleus 658) to dampen the sound. Signal processing to the actuator 656 is used to maintain the average sound level to a safe-comfortable average level (e.g., 60 db).

The ear collar 650 can also be used to support a sound level responsive diaphragm (in place of or in addition to the actuator)(not shown). High sound levels would cause the diaphragm to close and reduce the vibration delivered to the ossicular chain. Lastly, the ear collar 650 can have a further portion that covers the ear canal side of the tympanic membrane 654. The further portion would have a cavity having a rheological material disposed therein that is activated by any of the activation means discussed above and preferably separately from the activation of the ear collar portion. The further portion covering the tympanic membrane 654 can also be disposed in the ear canal as a separate element without an ear collar portion. The rheological material in the further portion can be selectively activated to become stiff and thereby dampen high noise levels.

Figure 7A:
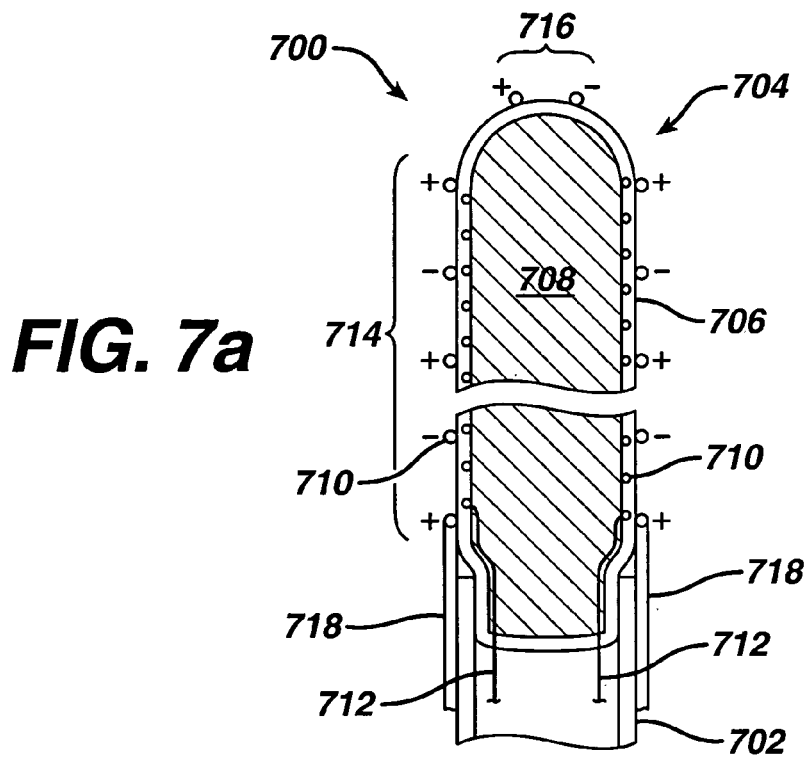
FIG. 7a illustrates an electrosurgical device configured as a linear ablative probe (LAP).
Figure 7B:
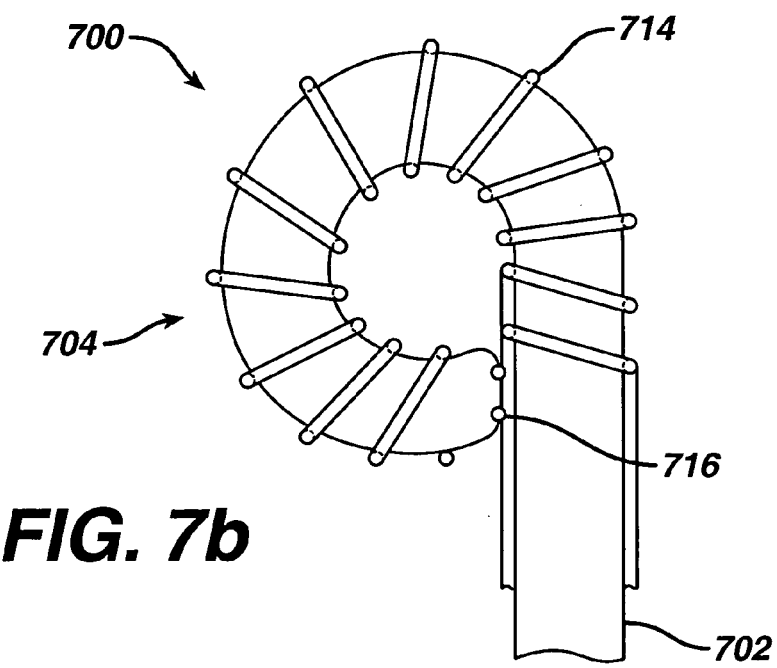
FIG. 7b illustrates the device of FIG. 7a configured as a circular ablative probe (CAP).

Referring now to FIGS. 7a and 7b, there is illustrated an electrosurgical instrument for use in certain surgical procedures, the electrosurgical instrument being generally referred to by reference numeral 700. Certain surgical procedures require both a circular ablation and a linear ablation. For example, in certain surgical procedures involving the heart, a circular ablative probe (CAP) is used to make a circular ablation around a pulmonary vein (PV) and a linear ablative probe (LAP) is used to make a linear ablation from the PV to the mitral valve. Therefore, both a CAP and a LAP are needed for such procedures. The electrosurgical instrument 700 illustrated in FIGS. 7a and 7b provides a single instrument capable of making both a linear and circular ablation.

The electrosurgical instrument 700 includes a tubular body 702, at a distal end of which is an articulatable tip 704. The articulatable tip 704 has a flexible bladder 706, preferably fabricated from an elastomer, that defines a cavity 708. The flexible bladder is disposed at a distal end of the tubular body 702, and is preferably adhered to the tubular body with an adhesive. A rheological material, such as a MR fluid is disposed in the cavity 708. The MR fluid is preferably activated by a magnetic field generated by applying a current to conductive coils 710 via leads 712. The coils 710 are preferably embedded in the walls of the flexible bladder 706. The articulatable tip 704 also includes two sets of electrodes 714, 716, each of which preferably contain alternating electrodes of different polarity (e.g., +, −).

In a LAP mode, the coils 710 are energized while the articulatable tip 704 is in a substantially straight position as is shown in FIG. 7a. This results in the MR material being activated, preferably, to a near solid state. The set of bipolar electrodes 716 on the distal most tip of the articulatable tip 704 are energized via leads (not shown) to perform a linear ablation of intended tissue. The electrosurgical instrument 700 can be passed through a trocar in an endoscopic procedure or used in an open procedure.

In a CAP mode, the articulatable tip 704 is manipulated to the circular shape illustrated in FIG. 7b, at which time the coils 710 are energized to activate the MR fluid to a desired state, preferably, a near solid. The articulatable tip can be manipulated by hand in an open procedure or with graspers in an endoscopic procedure. After the articulatable tip 704 has been manipulated and activated into the circular shape, the other set of electrodes 714 are energized via leads 718 to perform a circular ablation of intended tissue. Although, the electrosurgical instrument 700 has particular utility as a LAP or CAP, the articulatable tip 704 can be manipulated into other non-linear shapes and/or more than one linear segment. Those, skilled in the art will realize that the electrosurgical instrument 700 can utilize a smaller diameter trocar then what is possible for a CAP which does not have an articulatable tip 704 as discussed above. Furthermore, the articulatable tip 704 permits the use of a single instrument to replace two separate instruments (CAP and LAP) of the prior art.

Although described with regard to a MR fluid and an electromagnet activation means, those skilled in the art will realize that the surgical-instrument 700 can utilize other rheological materials and/or means for activation thereof. Furthermore, the electromagnetic field required to activate the magnetorheological material can be created (partially or fully) by the electrical energy being used for ablation. For instance, if the ablation is by RF energy, the electrical conductors could also be wrapped as a coil around the flexible bladder. Therefore, the directional electromagnetic field created by the passage of the ablation current can itself be used to activate the MR fluid to a desired state. Additionally, a pre-shaped stylet can be placed inside a hollow area to conform the shape of the flexible bladder thereto. Subsequently, the rheological material can be activated in the shape dictated by the stylet. Lastly, a shape memory material, such as Nitonal, can be used in the instrument. The shape memory material can be heated, preferably by electrical resistance, into a memorized shape. Although the shape memory alloy cannot provide rigidity, it can shape the distal end of the instrument to a desired shape after which the rheological material can be activated to provide the necessary rigidity.

Referring now to FIGS. 8a, 8b, 8c, and 8d, there are illustrated examples of instruments that are capable or collapsing and expanding. During minimally invasive surgery it is often necessary to deliver an instrument, or perform a procedure, through a limited size opening or into a confined space where mobility is limited. The instruments illustrated in FIGS. 8a, 8b, 8c, and 8d are examples of instruments that provide the ability to deliver an instrument in a first deliverable state, convert it into a second working state, and then reconvert it to the first state for removal. In the prior art, instruments were provided with means (e.g., hinges, shape memory alloys, plastically deformable shafts, etc.) to be folded, bent, or inflated with gas or saline into a delivery state and then unfolded, bent in situ, or deflated for performance of their function.

Referring now to FIGS. 8a and 8b in particular, there is illustrated an example of an electrosurgical instrument capable of having collapsed and expanded shapes, the instrument being generally referred to by reference numeral 800. The instrument 800 is shown in FIG. 8a in a collapsed state and being passed through a trocar tube 802. The instrument 800 has at least a portion thereof, preferably an end-effector 804, disposed at a distal end portion of the instrument 800. The end-effector 804 has a flexible bladder 806 that defines a cavity 808. The flexible bladder 808 is preferably attached to a tubular body 809 by any means known in the art, such as by adhesive. The cavity is in fluid communication with a source 813 of rheological material 810, preferably through a lumen 811 in the tubular body 809. The rheological material 810 is preferably a MR fluid. The source 813 of rheological material 810 is preferably a squeeze bulb that is also used to deliver the rheological material into the cavity 808, however, other means, such as a pump (not shown) or syringe (not shown) can also be used to deliver the rheological material 810 into the cavity 808. While the rheological material 801 is withdrawn from or otherwise absent from the end-effector 804, the same is in a collapsed state and capable of being passed through the trocar 802, as is illustrated in FIG. 8a.

Similarly to the surgical instrument 700 discussed above with regard to FIGS. 7a and 7b, the end-effector has an activation means for activating a MR fluid. As discussed above with regard to FIGS. 7a and 7b, the activation means is preferably at least one conductive coil (not shown) embedded in the walls of the flexible bladder for generating a magnetic field with the application of a current through the conductive coils.

Referring now to FIG. 8b, after the end effector 804 has passed through the trocar 802, the MR fluid 810 is delivered to the cavity 808 of the flexible bladder 806 from the source 813 by the squeeze bulb or other delivery means. The pressure of the MR fluid 810 in the flexible bladder 806 expands the end-effector 804 into an expanded shape, such as an umbrella shape as illustrated in FIG. 8b. Those skilled in the art will appreciate that numerous shapes are possible for the end-effector 804. While the flexible bladder 806 is pressurized with the MR fluid 810, it is activated, preferably by energizing the conductive coils to attain a desired state, preferably a near solid state. The end-effector 804 also preferably has a means for cauterizing tissue, such as electrodes 814 disposed on a surface of the end-effector for supplying radio frequency energy. The electrodes 814 are preferably bipolar electrodes (e.g., +, −) arranged in alternating polarity.

Figure 8C:
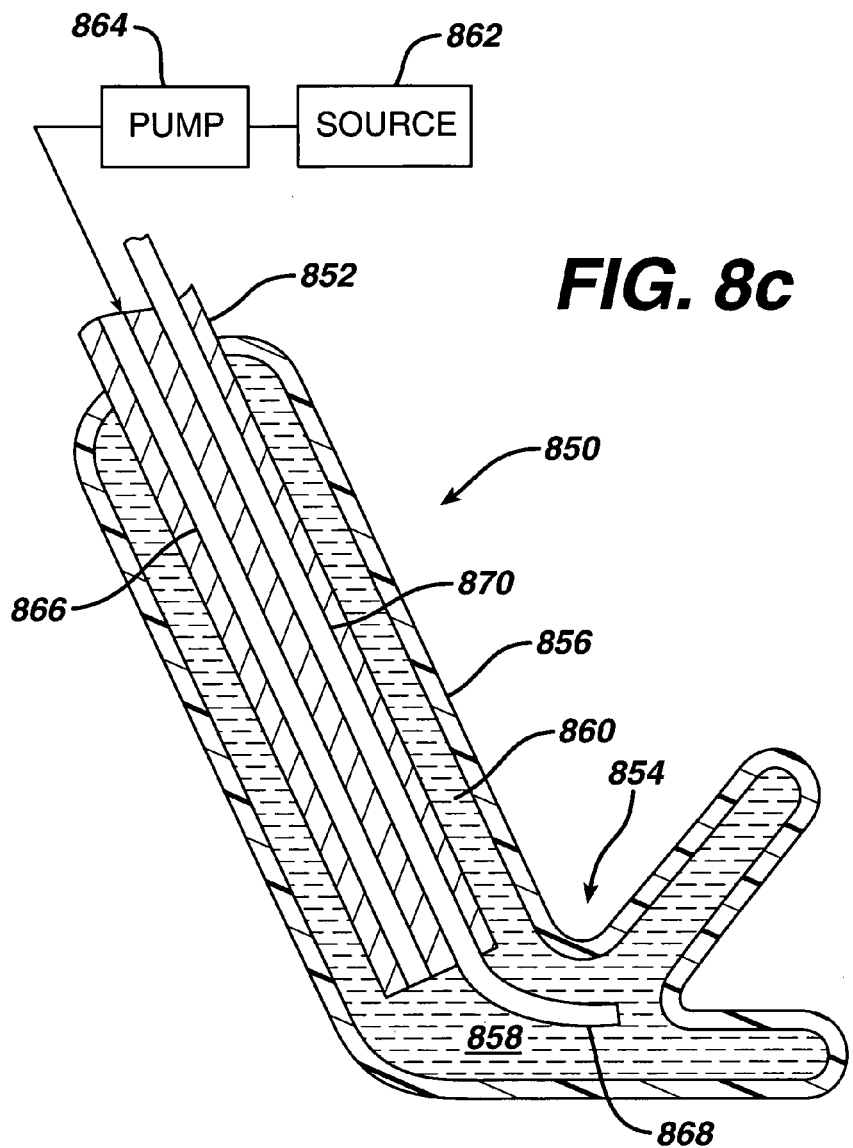
FIG. 8c illustrates a section view of an anastomotic stabilizer in an expanded state.
Figure 8D:
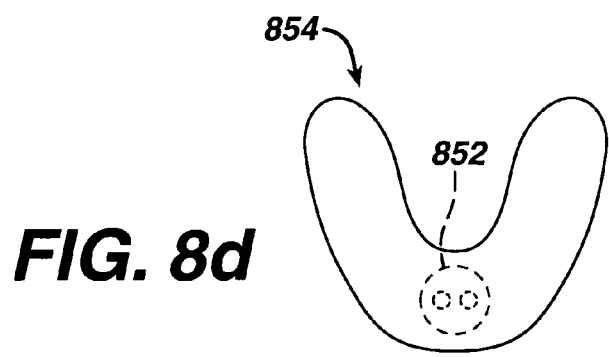
FIG. 8d illustrates an end view of the anastomotic stabilizer of FIG. 8c.

Referring now to FIGS. 8c and 8d, there is illustrated an anastomotic stabilizer 850, useful in a coronary artery bypass graft (GABG) procedure and shown in an expanded state. The anastomotic stabilizer 850 includes a tubular member 852 that is typically a rigid member such as stainless steel. At a distal end of the tubular member 852 is an end effector 854 in the form of a forked member. The forked shape of the end effector 854 is shown clearly in FIG. 8d. The end effector 854 comprises a flexible bladder 856 of a flexible material. The flexible bladder 856 is attached to the distal end of the tubular member 852 and defines a cavity 858 having a rheological material 860 therein. The end-effector is shown in an expanded shape, after passage through a delivery instrument, such as a trocar. While being delivered, it is generally collapsed and has no or very little rheological material 860 in the cavity 858.

After delivery, rheological material 860, preferably a MR fluid is delivered into the cavity 858 from a source 862 via a delivery means, such as a pump 864. The delivery means and source are preferably integrated into a single element, such as a squeeze bulb or syringe. Preferably, the rheological material 860 is delivered into the cavity 858 by way of a first lumen 866 in the tubular member 852 that is in fluid communication at a first end with the source 862 and at a second end with the cavity 858. The delivery of the rheological material acts to expand the end-effector 854 into its desired shape, for example, into the forked shape anastomotic stabilizer. Subsequent to the expansion of the end-effector 854, the rheological material is activated by an activation means, which in the case where the rheological material is a MR fluid, is a means for generation of a magnetic field in the fluid. Preferably, the means for generation of a magnetic field comprises a flexible magnet 868 that is preferably delivered via a second lumen 870 in the tubular member 852.

Those skilled in the art will appreciate that a larger instrument can be passed through the trocar than would be possible if the instrument were not collapsible. Furthermore, although the end-effector 804, 854 is expanded, it is capable of being both rigid and solid, properties that are not achievable with devices of the prior art, such as balloons. Although described with regard to a MR fluid, those skilled in the art will realize that the surgical instruments 800, 850 can utilize other rheological materials and 49 or means for activation thereof. Furthermore, although the end-effectors have been described as being fully collapsible, portions thereof may also be rigid.

Figure 9:
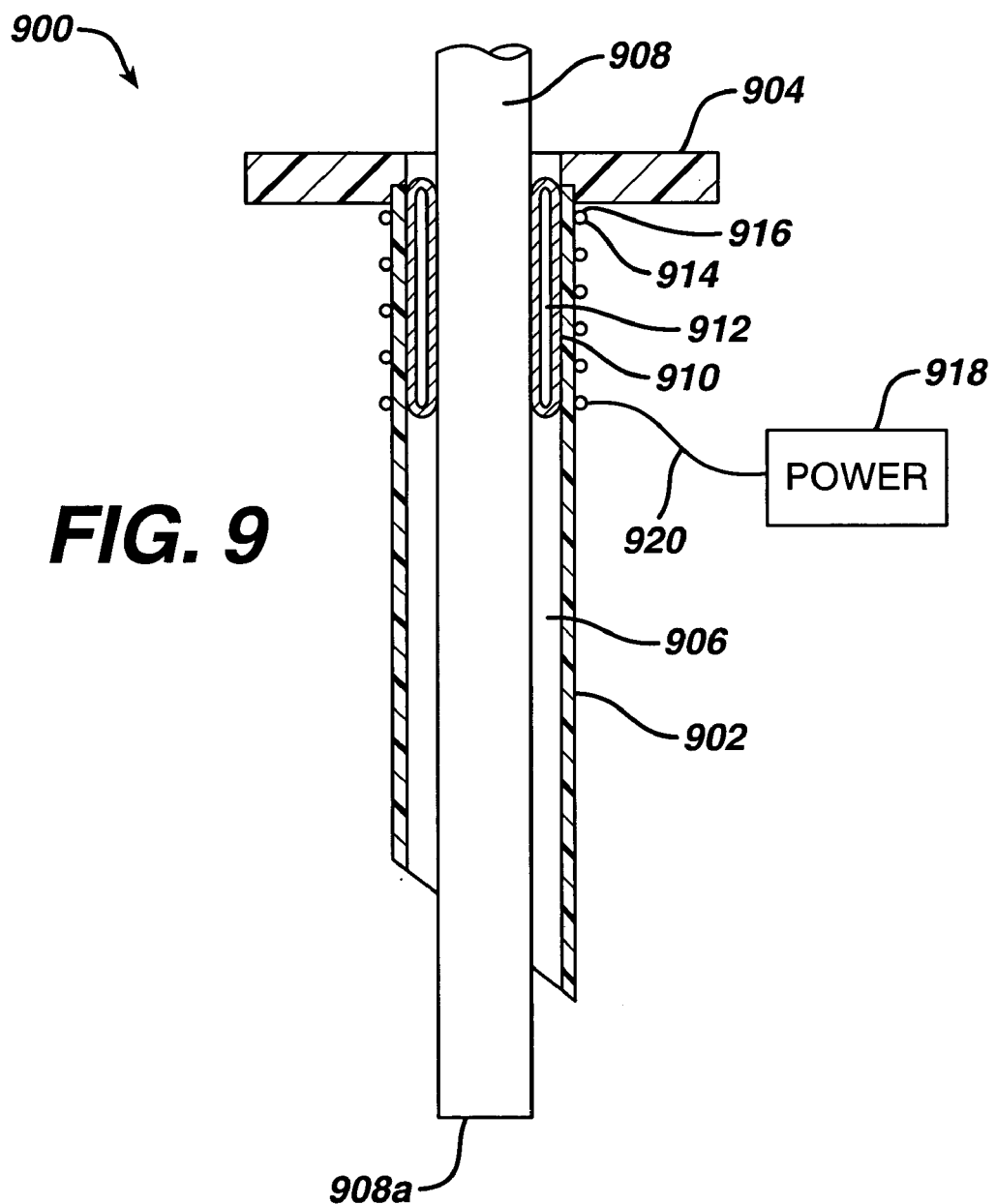
FIG. 9 illustrates a sectional view of a trocar having a doughnut shaped flexible bladder filled with a rheological material.

Referring now to FIG. 9 there is illustrated a trocar for use in minimally or less invasive surgery, the trocar being generally referred to by reference numeral 900. The trocar 900 generally has a tubular body 902 and a disc shaped port 904. Although the trocar can be fabricated from a rigid material, such as stainless steel, it is preferred that at least the tubular body 902 be fabricated from a flexible material, such as a thermoplastic or elastomer. The tubular body 902 defines a lumen 906 for passage of a surgical instrument 908. In at least a portion of the lumen 906 is disposed a flexible bladder 910 defining a cavity 912 and having a rheological material 914, preferably, a MR fluid, disposed therein. Preferably, the flexible bladder 910 has a doughnut or elongated doughnut shape. A means for activating the rheological material is provided, preferably in the form of at least one coil of electrical conductors 916. The coil of conductors 916 is preferably adhered to an outer wall of the tubular body 902 and is insulated to prevent an electrical shock to an operator or patient. The coil of conductors is energized by the supply of power from a power supply 918 via leads 920.

The surgical instrument 908 is intended to have a snug fit inside the flexible bladder 910 as is shown in FIG. 9. Since, the tubular body 902 is flexible, the surgical instrument 908 can be easily manipulated in the trocar 900 when the rheological material 914 is in a liquid state. After the surgical instrument 908 is positioned in a desired orientation, the rheological material 914 in the cavity 912 of the flexible bladder 910 can be activated to change the state of the rheological material to that desired from a gel to a near solid. Thus, the trocar can serve to reduce or prevent a tremor in a surgeon's hand from being translated to the distal end 908*a* of the surgical instrument 908. In effect, the flexible bladder 910 acts as a mechanical filter wherein displacements requiring low forces would be prevented, and only deliberate movements would be allowed. Although described with regard to a magnetorheological fluid and an electromagnet activation means, those skilled in the art will realize that the trocar 900 can utilize other rheological materials and/or means for activation thereof.

Figure 10:
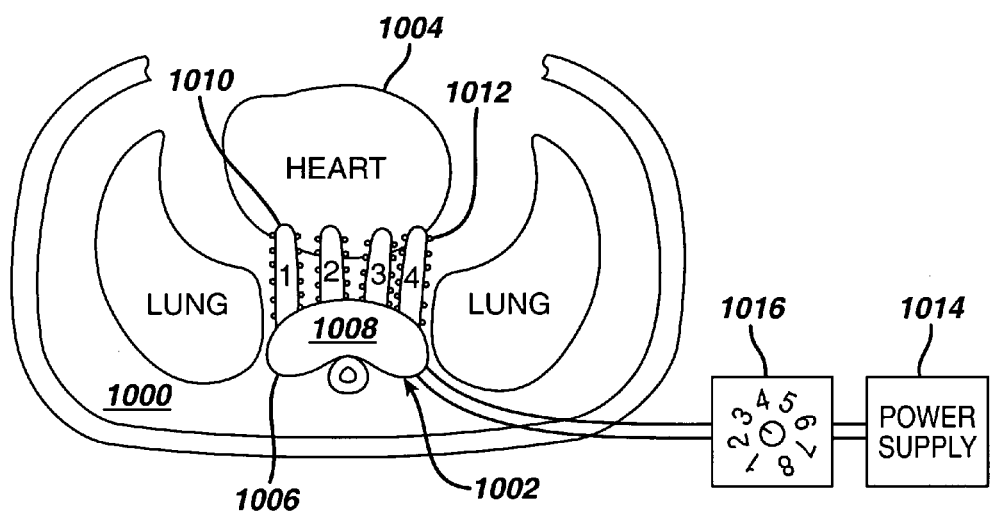
FIG. 10 illustrates a sectional view of the chest cavity having a support sac shown supporting the heart.

Referring now to FIG. 10 there is shown an outline of a chest cavity 1000. The chest cavity 1000 having a support sac 1002 disposed therein for supporting and/or lifting the heart 1004. Although the support sac 1002 is described by way of lifting and/or supporting the heart in the chest cavity, such is given by way of example only and not to limit the scope or spirit of the present invention. Those skilled in the art will appreciate that the support sac 1002 can be used to lift, rotate, and/or support other organs or bodily features as well as in other non-medical applications.

The support sac 1002 has a flexible bladder 1006 that is filled with a rheological material 1008, preferably a MR fluid. The support sac 1002 can be prefilled with the rheological material. Alternatively, the support sac 1002 can be empty or partially filled with the rheological material that permits its delivery to an intended site through a delivery means, such as a trocar tube. In the alternative version, once it is in the intended site, the rheological material 1008 is delivered to the flexible bladder 1006 through a delivery means (not shown) such as a pump or squeeze bulb.

The flexible bladder 1006 preferably includes arms 1010, preferably a plurality of arms 1010 which also have the rheological material 1008 therein. Each of the arms 1010 has a means for activating the rheological material therein. Preferably, the means for activation can selectively activate the rheological material in each of the arms 1010. In the case where a MR fluid is utilized, the means for activation comprises a means for generating a magnetic field in the MR fluid, such as conductor coils 1012 corresponding to each arm 1010. The conductor coils 1012 are preferably connected to a battery supply 1014, such as a battery, via a switching unit 1016. The switching unit 1016 preferably selectively energizes the conductor coils 1012 corresponding to the arms 1010 whereby the selected conductor coils 1012 remain energized as subsequent conductor coils 1012 are selected.

In operation, particularly in heart surgery where a lower portion of the heart is not easily accessible, the support sac 1002 is delivered to the intended site, either placed in an open procedure or delivered through a delivery means in a less invasive procedure. The heart 1004 is lifted and/or rotated to an appropriate position and each of the arms 1010 are lifted into a support and/or lift position and selectively energized through the switching means 1016 to activate the arms 1010 to a near solid state. In such a state, the arms 1010 are capable of lifting and/or supporting the heart 1004. Although described with regard to a MR fluid and an electromagnet activation means, those skilled in the art will realize that the support sac 1002 can utilize other rheological materials and/or means for activation thereof.

Figure 11:
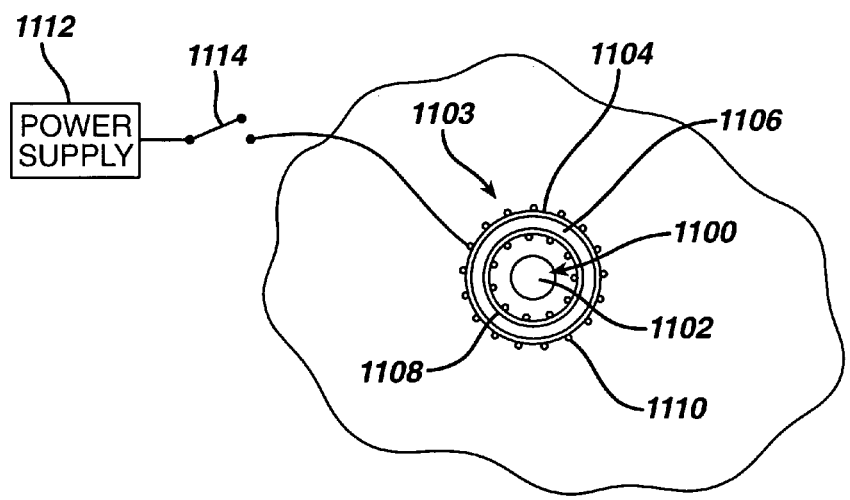
FIG. 11 illustrates a sphincter muscle and a sphincter implant device.

Referring now to FIG. 11, there is illustrated an outline of a sphincter muscle 1100. The sphincter muscle 1100 is a circular muscle that constricts an orifice 1102. Implanted around the sphincter muscle 1100 is a doughnut shaped implant 1103. The implant has a flexible bladder 1104 defining an annular cavity 1106. The cavity 1106 has a rheological material 1108 disposed therein, preferably a MR material. The implant 1103 further has a means for activating the rheological material 1108. Preferably, a conductive coil 1110 disposed in the flexible bladder is used to generate a magnetic field in the rheological material 1108. However, a magnet (not shown) can also be used. Power is supplied to the conductive coil 1110 by a power supply 1112, such as a battery, via a switch 1114. Optionally, a pumping means, such as a squeeze bulb (not shown) can be used to deliver the rheological material to the flexible bladder 1004.

In operation, the insert 1103 is preferably used in patients with an ostomy or with fecal/urinary incontinence for rapidly opening and closing the anal sphincter 1100 to maintain continence. When the rheological material 1108 is activated by closing the switch 1114, the sphincter becomes rigid and blocks fecal matter and/or fluid from passing. When the rheological material 1008 is inactivated by opening the switch 1114, the sphincter becomes relaxed and allows the patient to push fecal matter and/or fluid through the opening 1102. The hole in the middle of the doughnut shaped flexible bladder 1104 is sized such that fecal matter and/or fluids will not pass when the rheological material is activated to a desired state yet allows fecal matter and/or fluids to be pushed through when the rheological material is inactivated. The constriction of the opening 1102 can be amplified by pumping rheological material into the cavity to expand the flexible bladder and thereby decrease the size of the hole in the middle of the doughnut shaped flexible bladder 1104. Although described with regard to a MR fluid and an electromagnet activation means, those skilled in the art will realize that the implant 1103 can utilize other rheological materials and/or means for activation thereof. Furthermore, such means can also be implanted and accessed through the skin.

Figure 12:
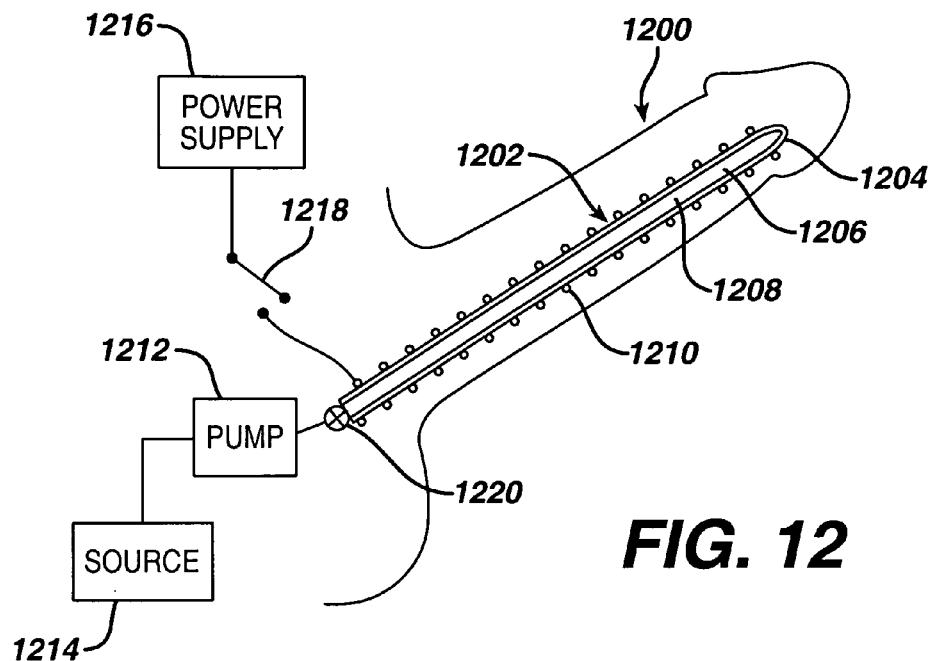
FIG. 12 illustrates an outline of a penis having a penile implant therein.

Referring now to FIG. 12, there is illustrated a penis 1200 having a penile implant 1202 implanted therein. The penile implant 1202 is implanted in a similar manner and in a similar location as those known in the art. The penile implant 1202 comprises a flexible bladder 1204 that defines a cavity 1206. A rheological material 1208, preferably a MR fluid is disposed in the cavity 1206. The penile implant 1202 further comprises a means for activating the rheological material 1208. The means for activating preferably comprises a conductive coil 1210 disposed on the flexible bladder 1204.

Also provided is a delivery means, such as a pump 1212 for delivering the rheological material 1208 from a source 1214 of rheological fluid. Preferably, the pump 1212 and source 1214 comprise a squeeze bulb that is implanted under the skin or in the scrotum. Thus, the penile implant operates in a similar manner to penile implants known in the art that utilize saline solution. However, unlike the penile implants that utilize saline solution, after the flexible bladder 1204 is filled with the rheological material 1208, it can be activated to add rigidity to the implant 1202.

In operation, the penile implant provides an erection by pressurizing the flexible bladder 1204 with rheological material by withdrawing the same from the source 1214 and delivering it to the flexible bladder 1204 by way of the pump 1212. Preferably, this is accomplished by squeezing a squeeze bulb. After the flexible bladder 1204 is pressurized, the rheological material is activated to a desired state, preferably a near solid. The activation is preferably done by generating a magnetic field in a MR fluid, such as by passing a current through the conductive coil 1210 from a power supply 1216 via a switch 1218. When an erection is no longer desired, the switch 1218 is open to inactivate the rheological fluid and a valve 1220 is used to return the rheological fluid to the source 1214. Like the pump 1212 and source 1214, the power supply 1216, switch 1218, and/or valve 1210 can also be implanted under the skin. Although described with regard to a MR fluid and an electromagnet activation means, those skilled in the art will realize that the penile implant 1202 can utilize other rheological materials and/or means for activation thereof.

Figure 13A:
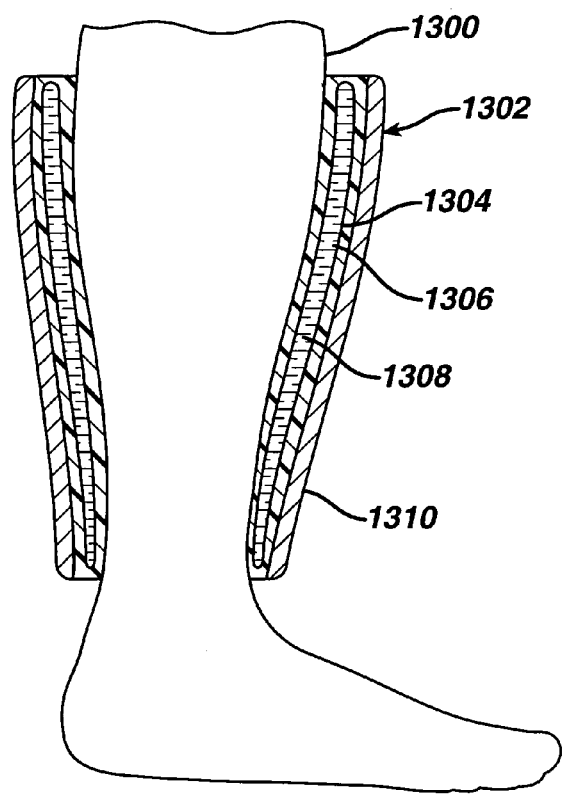
FIG. 13a illustrates an outline of a person's foot and lower leg having a cast/splint thereon, the cast/splint having a flexible bladder defining a cavity and an MR or ER fluid disposed in the cavity.

Referring now to FIG. 13*a*, there is illustrated an outline of a person's foot and lower leg 1300 having a splint or cast 1302 thereon, collectively referred to hereinafter as a cast. The cast 1302 has a flexible bladder 1304 that defines a cavity 1306. Either an ER or a MR fluid 1308 is disposed in at least a portion of the cavity 1306. Preferably a MR fluid 1308 is used. The flexible bladder 1304 is preferably in a sheet form and is wrapped around the lower leg 1300 and fixed at a seam by any means known in the art, such as by Velcro, straps, tape, or the like.

The cast 1302 further has an activation means for generating a magnetic field in the MR fluid and thereby activating the MR fluid to a desired state, preferably, to a near solid state. The activation means preferably comprises a flexible magnet 1310 that is wrapped around the flexible bladder 1304. As discussed above with regard to the shoe insert, the cast 1302 can have means for activating and inactivating the rheological fluid to thereby massage the body part to which it is disposed.

In operation, the flexible bladder 1304 is tightly wrapped around the lower leg 1300 or other body part to be fixed and/or massaged and the ends thereof fixed as discussed above. The flexible magnet 1310 is then also wrapped around the flexible bladder 1304 and its ends fixed in a similar fashion. Although a flexible magnet is preferred, one or more rigid magnets (not shown) may be used and disposed in pockets (not shown) in the flexible bladder 1304. The magnet 1310 activates the magnetorheological material to a desired state, preferably a near solid state to provide the rigidity of a cast.

Figure 13B:
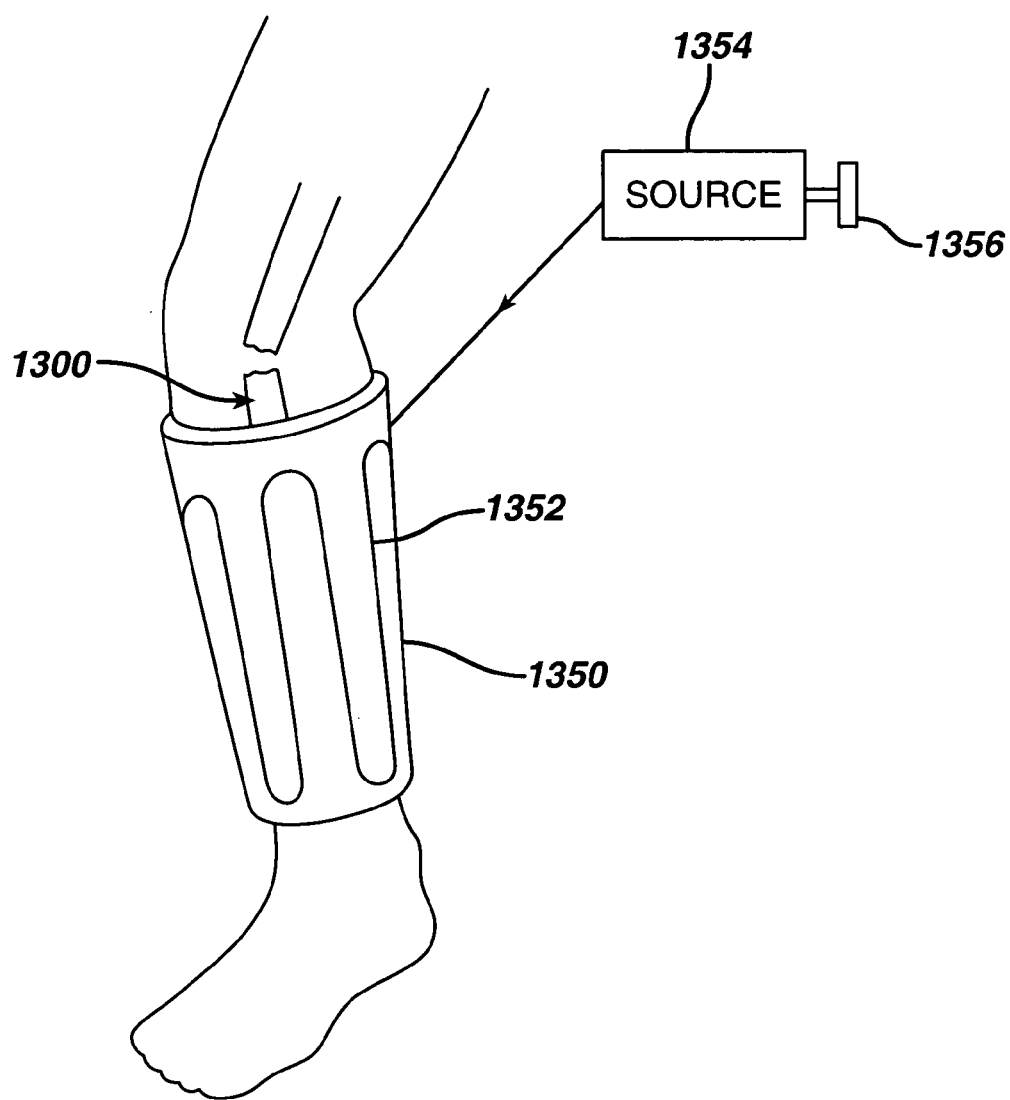

Referring now to FIG. 13*b*, there is illustrated an alternative version of the cast of FIG. 13*a*, the cast of FIG. 13*b* being generally referred to by reference number 1350. The cast 1350 has a flexible bladder similar to that described with regard to cast 1302. However, the means for generation of a magnetic field in the MR fluid is by means of an electromagnet 1352 and a power source 1354. Preferably, the power source has an adjustment means, such as a knob 1356 to control the magnitude of the current supplied to the electromagnet 1352 so as to selectively activate the MR fluid to a desired state.

If a massaging action is desired, a processor and power supply (not shown) are provided and configured similarly to that described above with regard to the shoe insert.

In both versions of the cast, it is preferred that the activation of the MR fluid is to a near solid state to provide the rigidity of a cast. However, unlike the rigid cast of the prior art, the casts 1302, 1350 of the present invention can be temporarily relaxed from the rigid state or even temporarily removed. Furthermore, the cast 1302 is easily removed without saws or the like. In addition, during rehabilitation, the shape and rigidity of the cast can be varied as necessary by inactivating and reactivating the rheological fluid.

Figure 14A:
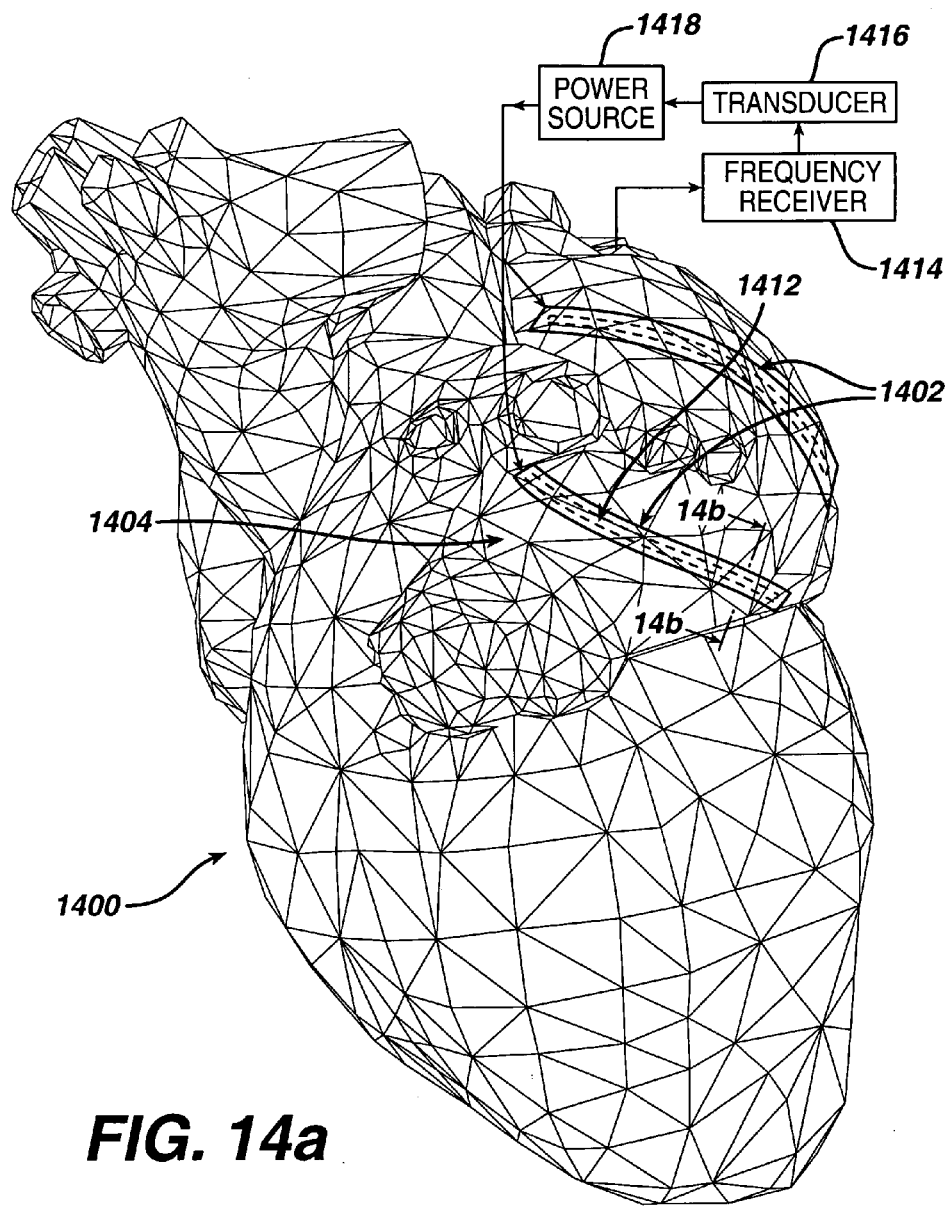
FIG. 14a illustrates an outline of a heart having at least one atrial fibrillation restraining means disposed therein.
Figure 14B:
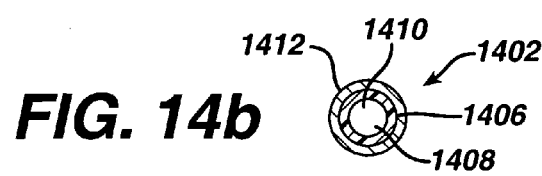
FIG. 14b illustrates a sectional view of the atrial fibrillation restraining means of FIG. 14a as taken along line 14b-14b therein.

Referring now to FIG. 14*a*, there is shown an outline of the heart 1400 having at least one and preferably two atrial fibrillation (AF) restraining means 1402 disposed in the left ventricle 1404 of the heart 1400. Referring now to FIG. 14*b*, the AF restraining means 1402 preferably comprises a flexible bladder 1406 fabricated of a flexible material. The flexible bladder 1406 defines a cavity 1408 in which a rheological material 1410, preferably a MR fluid, is disposed. An electromagnet in the form of a conductor coil 1412 is disposed on the flexible bladder 1406 to generate a magnetic field in the rheological material to change it to a desired state.

The operation of the AF restraining means will now be described with reference to FIG. 14*a*. If the heart starts fibrillating, a frequency receiver 1414 senses a frequency of the fibrillation and outputs a signal corresponding to the frequency to a transducer 1416. The transducer 1416 converts the frequency response of the frequency receiver 1414 into a digital signal. If the frequency of the fibrillation is greater than a predetermined threshold, the transducer 1416 controls a power output from a power source 1418 to the conductor coils 1412 to each of the AF restraining devices. In response to the power output, the MR fluid is activated and the AF restraining means become rigid, thereby resisting the abnormal vibrations of the fibrillation of the heart and creates a resistance for arrhythmia.

Figure 15A:
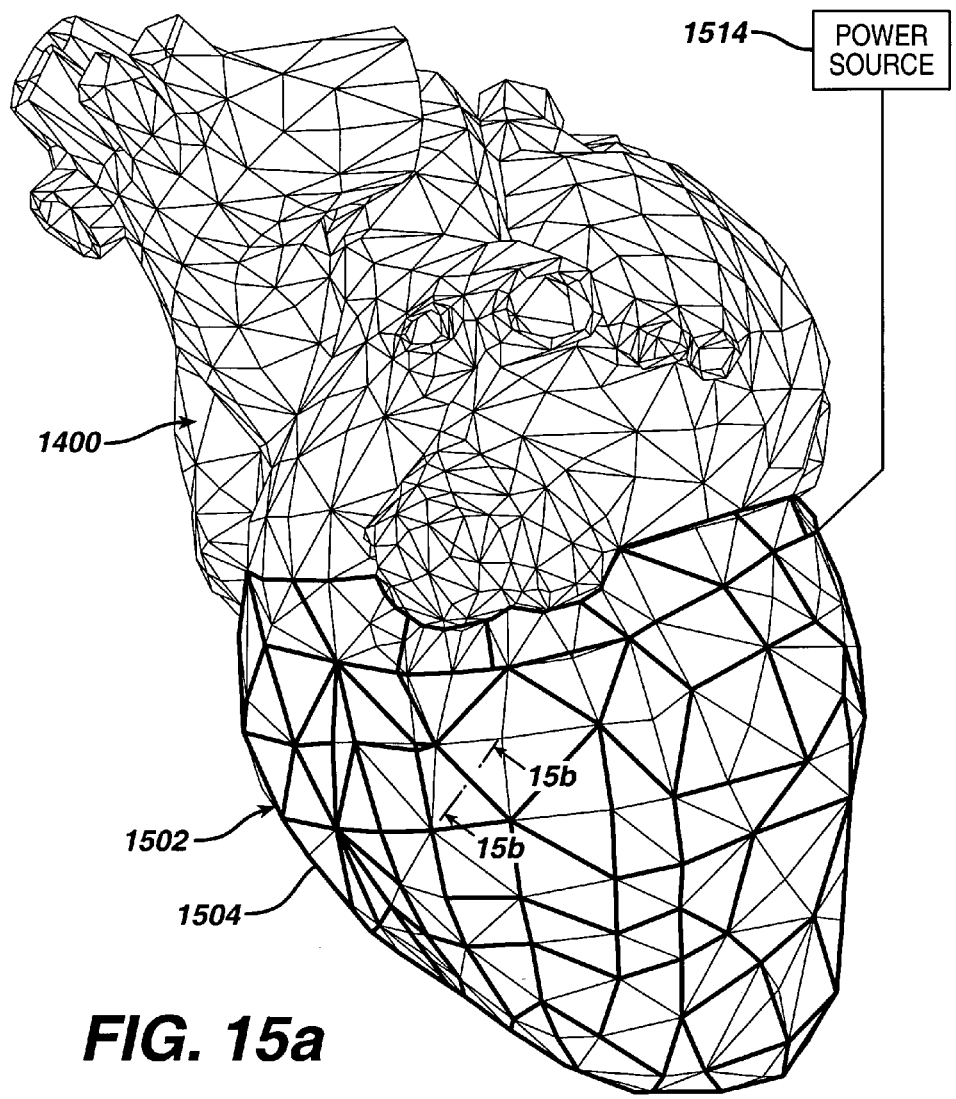
FIG. 15a illustrates a heart having an expansion prevention means disposed thereon.

Referring now to FIG. 15*a*, there is illustrated the outline of the heart 1400 and having an organ/conduit restriction means (hereinafter collectively referred to as an organ restriction means). Although the organ restriction means has particular utility with regard to the heart 1400, it is applicable to numerous and various types of organs and conduits. Therefore, without limiting the applicability of the invention to the heart, the organ restriction means will first be described in such environment.

Figure 15B:
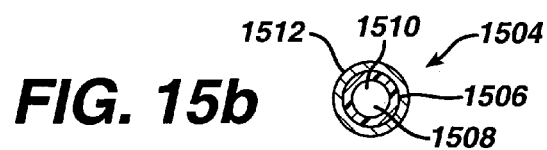
FIG. 15b illustrates a sectional view of the expansion prevention means of FIGS. 15a and 16 as taken along line 15b-15b in FIGS. 15a and 16.

The organ restriction means comprises a mesh 1502 of fine tubular members 1504. The mesh 1502 is disposed on at least a portion of the heart 1400, such as the ventricles. Referring now to FIG. 15*b*, each of the tubular members 1504 comprises a flexible bladder 1506 fabricated from a flexible material. The flexible bladder 1506 defines a cavity 1508 in which a rheological material 1510, preferably a MR fluid, is disposed. A conductor coil 1512 disposed on each of the tubular members 1504 or around the mesh 1502 is used to generate a magnetic field in the rheological material 1510.

The operation of the organ restriction means will now be described with reference to FIG. 15*a*. Upon a normal expansion and contraction of the heart 1400, the mesh 1502, being composed of flexible tubular members 1504, expands and contracts with the heart 1400. However, upon an abnormal expansion of the heart 1400, possibly caused by an aneurysm, blood pressure decreases thereby reducing the blood flow to the rest of the body. Either manually or automatically through a sensing means (not shown), when an abnormal expansion has begun, power is supplied to the conductive coils 1512 from a power source 1514 which in turn activates the rheological material in the tubular members 1504 to change the mesh 1502 to a relatively rigid structure, thereby restricting further expansion of the heart 1400.

The mesh 1502 may also be used with a pacing device (not shown). The pacing device responds to changes in the heart rate and strength of contraction and signals for the application of the magnetic field accordingly. The mesh 1502 may then selectively restrict or permit regulated (and physiologically normal) expansion and contraction of the ventricular walls. Additionally, the mesh 1502 may provide assistance with ejection, if provided with a means for delivering fluid (not shown) to the tubular members to expand the same and thereby squeeze the heart from the apex during systole.

Figure 16:
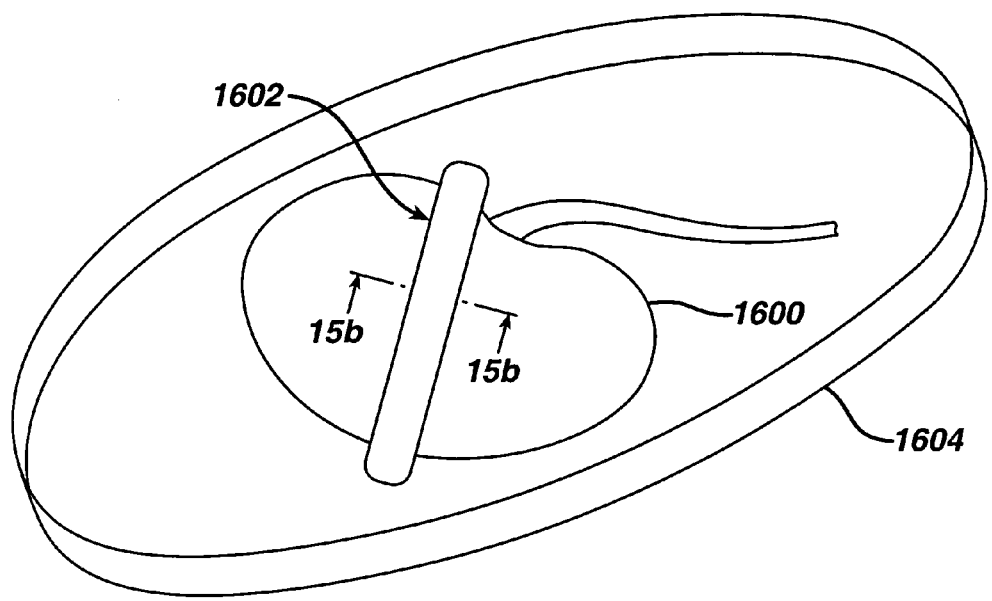
FIG. 16 illustrates an outline of a kidney having a variation of the expansion prevention means of FIG. 15a disposed on a portion thereof.

Referring now to FIG. 16, an alternative version of the organ restricting means is illustrated with regard to a kidney 1600, however, the organ restricting means may also be placed in a conduit or vessel, such as the ureter or urethra. The organ restricting means 1602 comprises a doughnut shaped flexible bladder having a similar configuration to that illustrated in FIG. 15b. In the alternative version, the rheological material is preferably a magnetorheological fluid which is activated by generation of a magnetic field therein. The magnetic field can be generated with an electromagnet or with a magnet, preferably worn as a belt 1604. While the belt 1604 is being worn, the rheological material is activated and the organ restricting means 1602 becomes rigid and thus does not allow for urination. When the belt 1604 is removed, the organ restricting means 1602 is relaxed, thus allowing for urination.

Figure 17:
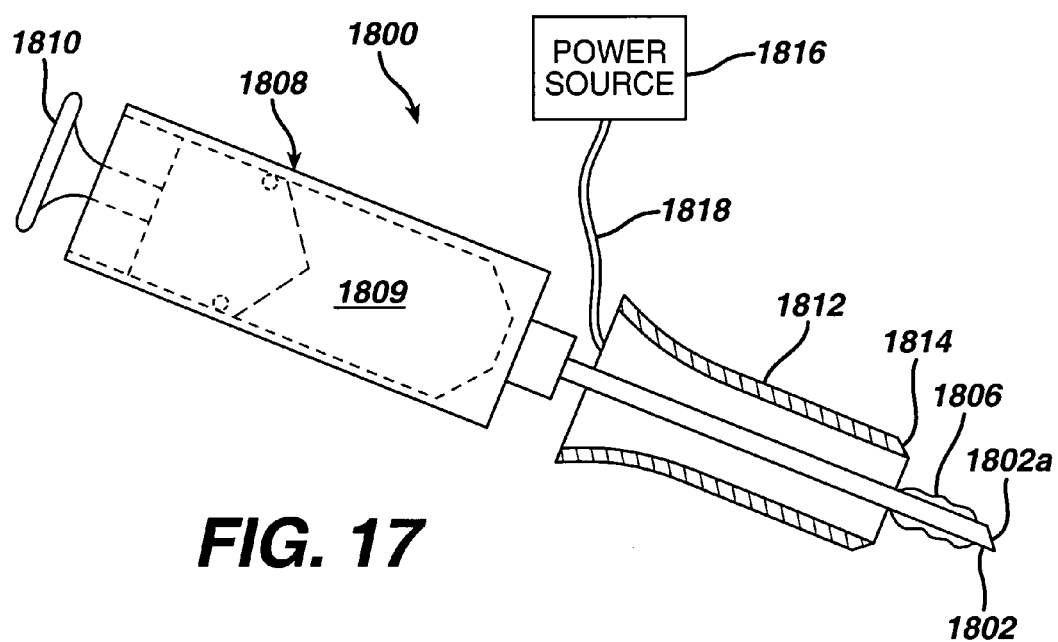
FIG. 17 illustrates a surgical punch for punching a hole in tissue.

Referring now to FIG. 17 there is illustrated a surgical punch for punching a hole in tissue, the punch being referred to generally by reference numeral 1800. The punch 1800 is particularly suited for punching holes in organs and vessels such as the aorta during a CABG procedure, however, it can be used for punching holes in any tissue and may also be configured for punching non-tissue, such as fabrics, leathers, papers and other sheet goods, all of which are collectively referred to as sheet members.

The punch 1800 has a needle 1802 for piercing the tissue 1804 to be punched. The needle 1802 has a sharp point 1802a at its distal end for facilitating the piercing of the tissue 1804. The needle 1802 further has a collapsible anvil 1806 disposed around its periphery near the distal end. The anvil 1806 comprises a flexible bladder. The flexible bladder defines a cavity that can be filled and drained of a rheological material, such as a MR material. The rheological material is preferably delivered to the cavity by a lumen in the needle 1802. The lumen is preferably in fluid communication with both the cavity and a source of rheological material. Preferably, the source of rheological material is a syringe 1808 that not only stores the rheological material in the plunger body 1809 but includes a plunger 1810 used to both deliver and withdraw the rheological material into and from the cavity. The punch 1800 also includes a punch member 1812 having a cutting edge 1814 disposed at a distal end.

Figure 18A:
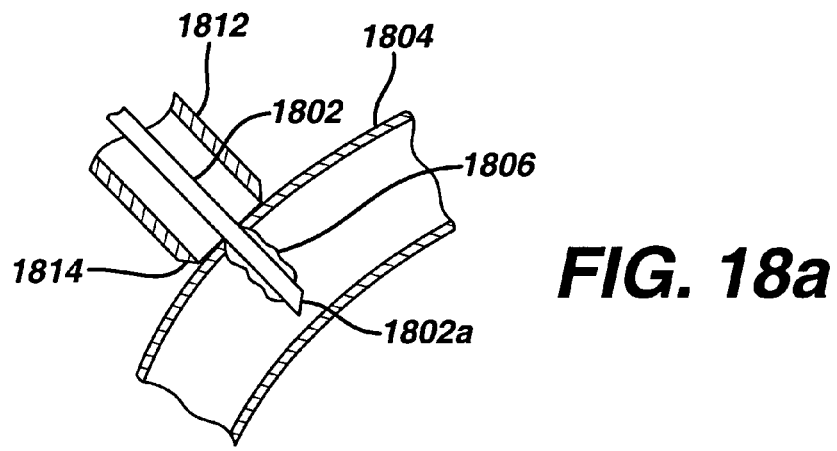
FIGS. 18a, 18b, and 18c illustrate the working end of the surgical punch of FIG. 17 in various states of use.
Figure 18B:
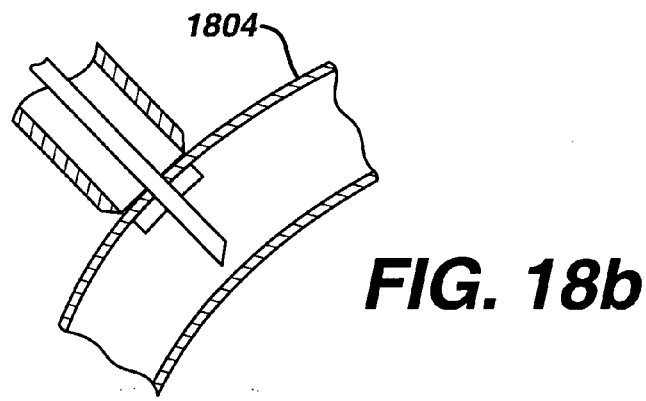
Figure 18C:
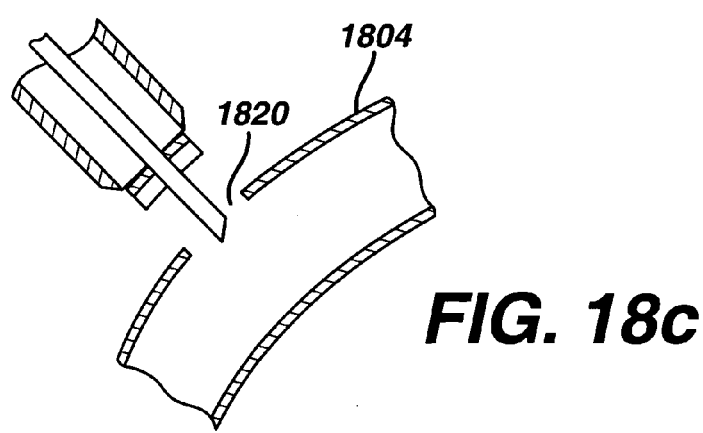

The operation of the punch 1800 will now be described with further reference to FIGS. 18a, 18b, and 18c. As shown in FIG. 18a, the sharp point 1802a of the needle 1802 is inserted through the tissue 1804 with the anvil 1806 collapsed such that the anvil 1806 passes through the tissue. As shown in FIG. 18b, the anvil 1806 is expanded by delivering the rheological material into the cavity, preferably by depressing the plunger 1810 of the syringe 1808 to force the rheological material from the plunger body 1809 and through the lumen of the needle 1802 and into the cavity. After the anvil 1806 is expanded, the rheological material therein is activated to a desired state, preferably, a near solid. Where the rheological material is a MR fluid, a magnetic field is generated in the MR fluid by a magnet (not shown) or by an electromagnet of conductor coils (not shown) disposed on the needle 1802 or flexible bladder which is powered by a power supply 1816 through leads 1820. Upon activation of the anvil 1806 the same becomes rigid and can be acted upon by the cutting edge 1814, as shown in FIG. 18c, to form a hole 1820 in the tissue 1804. The hole 1820 can be formed by urging the cutting edge 1814 against the anvil 1806 or by withdrawing the anvil 1806 into a bore 1822 of the punch member 1812. Although described with regard to a magnetorheological fluid and an electromagnet activation means, those skilled in the art will realize that the punch 1800 can utilize other rheological materials and/or means for activation thereof.

Figure 19A:
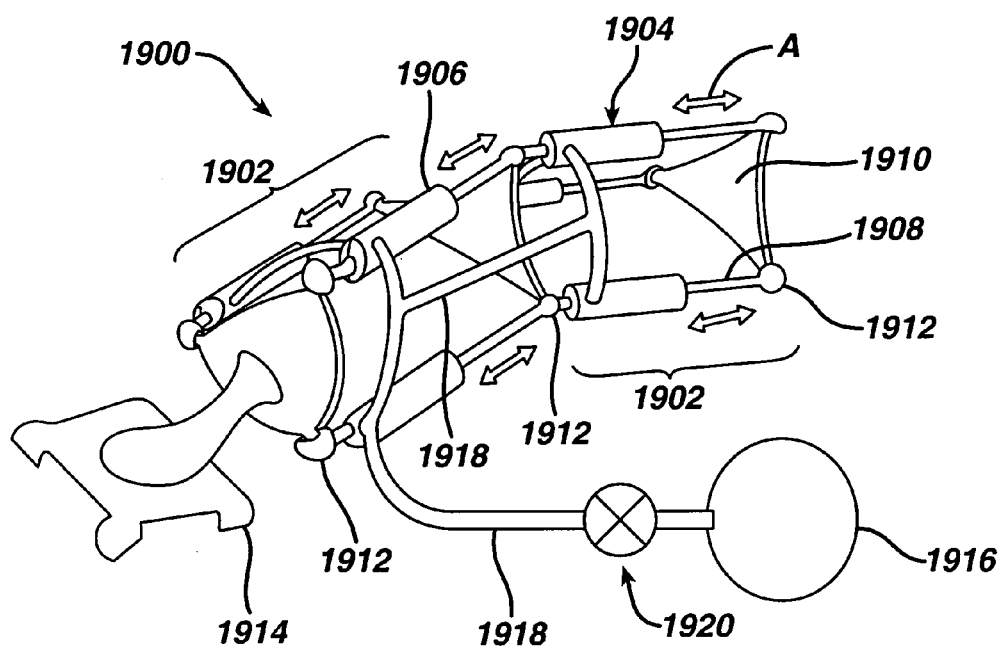
FIG. 19a illustrates a portion of a first variation of an articulatable shaft for use as a surgical stabilizer.
Figure 19B:
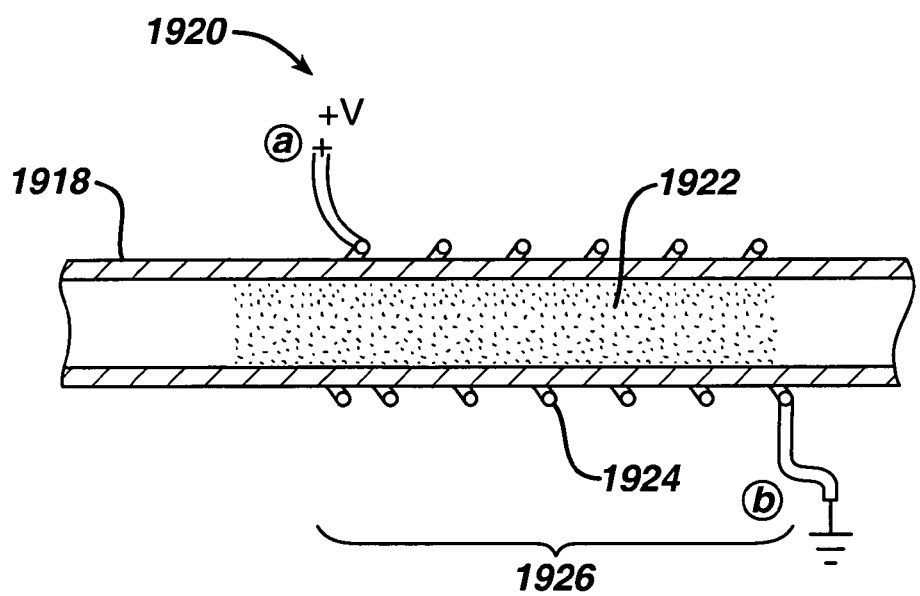
Figure 20:
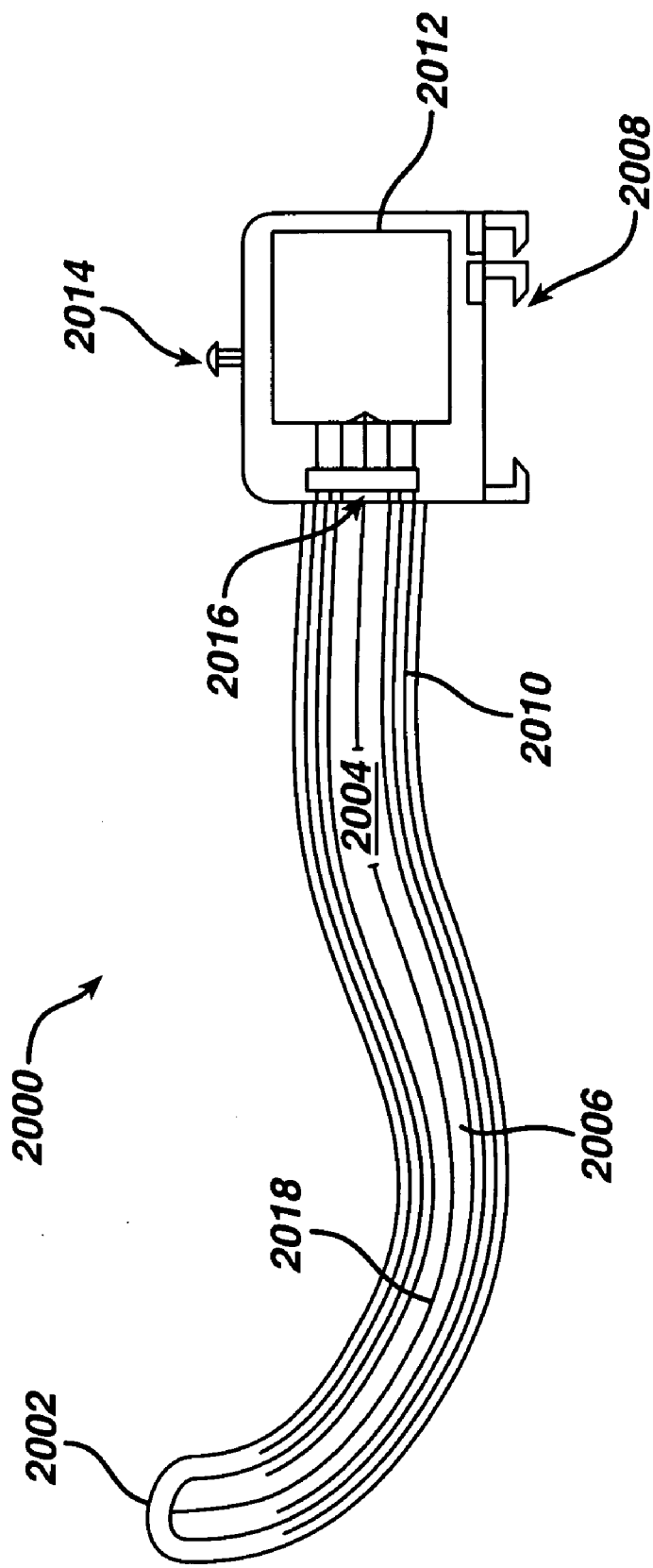
FIG. 20 illustrates a second variation of an articulatable shaft for use as a surgical stabilizer.

Rheological fluids can also be used to relax and stiffen shafts and other structures. In applications where a shaft or other structure needs to be positioned and subsequently locked into a position, rheological materials can be utilized in the shaft or portions thereof. FIGS. 19a, 19b and 20 describe two such applications for an articulatable shaft that is positioned and subsequently locked into the position. Although, these shafts have particular utility in the environment of surgical stabilizers, they are also useful for retracting, positioning, stretching, compressing, and dilating tissue, as well as in positioning of instruments or other devices attached thereto. The articulatable shafts may also be used to restrict or dampen motion, such as in artificial or robotic limbs.

Referring now to FIGS. 19a and 19b, there is illustrated a first version of a flexible shaft capable of being articulated into a desired position and locked into the desired position by activation of a rheological fluid. The shaft being generally referred to by reference numeral 1900 and illustrated by example only as a stabilizer for use in surgical procedures such as a CABG procedure. The shaft includes a plurality of links 1902, two of which are illustrated in FIG. 19a. Each link comprises one or more, and preferably a set of three extensible pistons 1904. Each of the pistons 1904 has a body 1906 in the form of a cylinder having a hydraulic or other incompressible fluid disposed therein. Each of the pistons 1904 further having a plunger rod 1908 extensible in direction A for interaction with the body as is known in the art.

Each of the pistons are disposed in at least two degrees of freedom, and preferably three degrees of freedom with respect to a link plate 1910 disposed between each link 1902. The three degrees of freedom are preferably supplied by way of a ball joint 1912 disposed at each end of the piston 1904. At a first end of the shaft 1900 can be disposed a base plate 1914 for attaching the shaft 1900 to another structure. At the other end of the shaft 1900 can be a tip (not shown) that interacts with tissue to stabilize or retract the same, or an adaptor (not shown) for connecting to another shaft, an instrument, a device, or other structure.

Each of the bodies 1906 of the pistons 1904 are fluidly connected such that the fluid disposed therein can be withdraw or added as necessary from a reservoir 1916 or another piston 1904 via appropriate tubing 1918. A valve 1920 is disposed in the tubing 1918 to either restrict or permit the flow of the fluid into or from the pistons 1904. In operation, the shaft 1900 is articulated into a desired position by manipulating the links 1902. As the links 1902 are articulated, the piston plunger 1908 either is pushed into the body 1906 or extended therefrom. When the plunger 1908 is extended, fluid is drawn into the body 1906 from the reservoir 1916 (or from another body 1906 from which fluid exits). When the plunger 1908 is pushed into the piston 1904, fluid is pushed from the body 1906 and into the reservoir 1916 (or to another body 1906 which draws in fluid). Those skilled in the art will appreciate that when the shaft 1900 is placed in a desired position and the valve 1920 is closed to not permit any fluid flow, the pistons 1904 will be locked in their positions, thereby locking the links 1902 and shaft 1900 composed thereof in the desired position. It will be appreciated by those skilled in the art that the stabilizer of FIG. 19a is only one illustrative example and that any structure whose internal volume changes with motion can be employed as links in the stabilizer arm with similar effect.

Referring now to FIG. 19b, there is illustrated a preferred implementation of the valve 1920. In the preferred implementation, the fluid disposed in at least a portion of the tubing 1918, is a rheological fluid 1922, preferably a MR fluid. A means for activating the MR fluid is also provided. Preferably, the means for activating comprises a conductive coil 1924 disposed around a portion 1926 of the tubing 1918. When a current is supplied to the coil 1924, the MR fluid 1922 is frozen to provide a plug that blocks any fluid flow in the tubing 1918. Alternatively, a magnet (not shown) can be placed in proximity to the portion 1926 of tubing 1918 to activate the MR fluid 1922.

Referring now to FIG. 20, there is shown another version of an articulatable shaft, generally referred to by reference numeral 2000. The shaft 2000 of FIG. 20 being configured as a tissue stabilizer. The shaft 2000 comprises a flexible cylindrical bladder 2002 defining a cavity 2004 having a rheological fluid 2006, preferably a MR fluid, disposed therein. The flexible bladder 2002 being connected at one end to a base 2008, such as a spring loaded base typically used for tissue stabilizers. The shaft 2000 includes a means for activating the MR fluid, preferably a conductive coil 2010 disposed or embedded in the flexible bladder 2002. The conductive coil 2010 is electrically connected to a power source 2012 preferably located in the base 2008. An on/off switch 2014 is provided to turn on and off the supply of power from the power source 2012 and a control knob 2016 is provided to vary the amount of current supplied from the power supply 2012 to the conductive coil 2010.

In operation, the switch 2014 is set in the off position or set in the on position with the control knob 2016 set at a low setting such that the shaft is articulatable. The shaft 2000 is manipulated into a desired position and the switch 2014 is either turned on or the control knob 2016 is turned up to supply additional power to activate the MR fluid 2006 to a desired state, preferably, to a near solid state. After activation of the MR fluid 2006, the shaft 2000 is locked into the desired position.

Also provided is a rheological fluid agitation means. A problem with rheological fluids has been that the particles suspended therein come out of the suspension over a period of time. To solve this problem, a vibrating member 2018 is preferably placed in the rheological fluid 2006 to agitate the suspension. The vibrating member 2018 is preferably a wire disposed in the rheological fluid 2006 and connected to a vibration generation means (not shown) to cause the wire to vibrate and agitate the fluid. The wire may also be used to activate the rheological material, such as by carrying a current. Although, the fluid agitation means is illustrated with regard to FIG. 20, it can be utilized in any of the embodiments disclosed herein. Alternatively, a source of vibration can be coupled to one end of the MR fluid cavity. This will generate vibration throughout the MR fluid by conduction of the vibration through the MR fluid.

Figure 21:
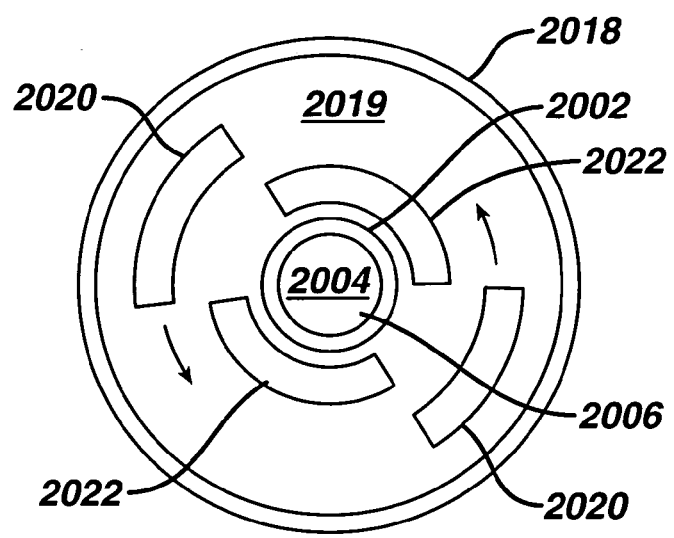
FIG. 21 illustrates an alternative activation means for the shaft of FIG. 20.

Referring now to FIG. 21, there is shown an alternative activation means for the shaft 2000 illustrated in FIG. 20. The activation means comprises an outer flexible bladder 2018 disposed around the flexible bladder 2002. In between the outer flexible bladder 2018 and the flexible bladder 2002 is an annular cavity 2019 in which is disposed rotatable magnets 2020 that rotate in the circumferential direction around the flexible bladder 2002. Also disposed in the annular cavity 2019 are stationary insulators 2022. The magnets 2020 and insulators 2022 are either a continuous flexible material or a plurality of segments to permit the necessary articulation of the flexible bladders 2002, 2018. A means (not shown) is provided to rotate the magnets 2020 between activation and inactivation positions.

FIG. 21 illustrates the activation position, in which the magnetic field generated from the magnets 2020 activate the magnetorheological fluid 2006 disposed in the cavity 2004 to thereby lock the shaft 2000 into the desired position. In the inactivated position (not shown) the magnets 2020 are rotated to align with the insulators 2022 to block the magnetic field and thereby inactivate the MR fluid 2006. Although the articulatable shafts 1900, 2000 have been described with regard to a MR fluid, an ER fluid may also be used.

Referring now to FIGS. 22a, 22b, 22c, and 22d there is illustrated a soft tissue retractor, generally referred to by reference numeral 2100. The soft tissue retractor 2100 comprises a flexible bladder 2102 that defines a cavity 2104. A rheological material 2106, preferably a MR fluid, is disposed in the cavity 2104. The soft tissue retractor 2100 further has a source 2108 for storing the rheological material 2106 and a means 2110 for delivering the stored rheological material. The source 2108 and delivery means 2110 preferably are combined in a single element, such as a squeeze bulb or syringe. A means for activating the rheological material 2106 in the cavity 2104 is also provided. Where the rheological material is a MR fluid, the means for activating the MR fluid is preferably an electromagnet comprising a conductive coil 2112 and a power source 2114 for delivering current to the coil 2112 via a switch 2116 and leads 2118.

Figure 22A:
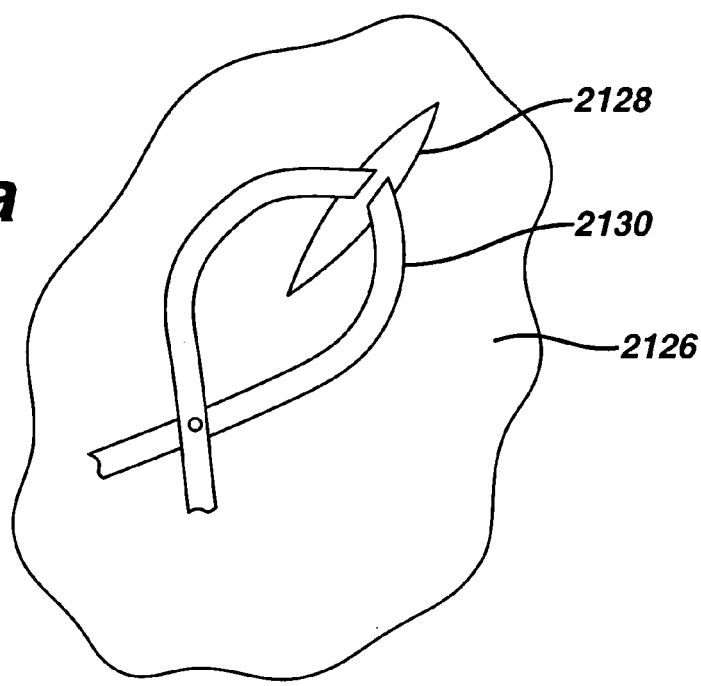
FIG. 22a illustrates an incision made in soft tissue and a mechanical retractor for opening the incision.
Figure 22B:
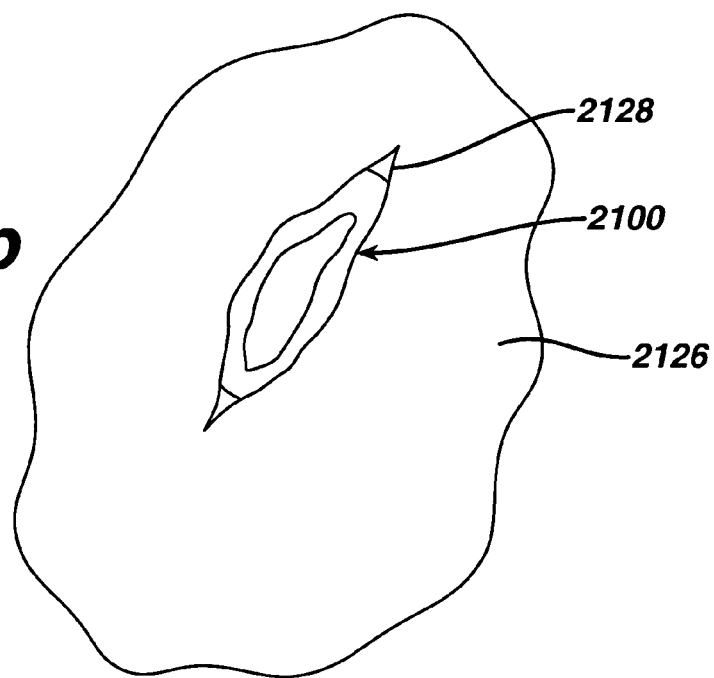
FIG. 22b illustrates a soft tissue retractor inserted into the incision.
Figure 22C:
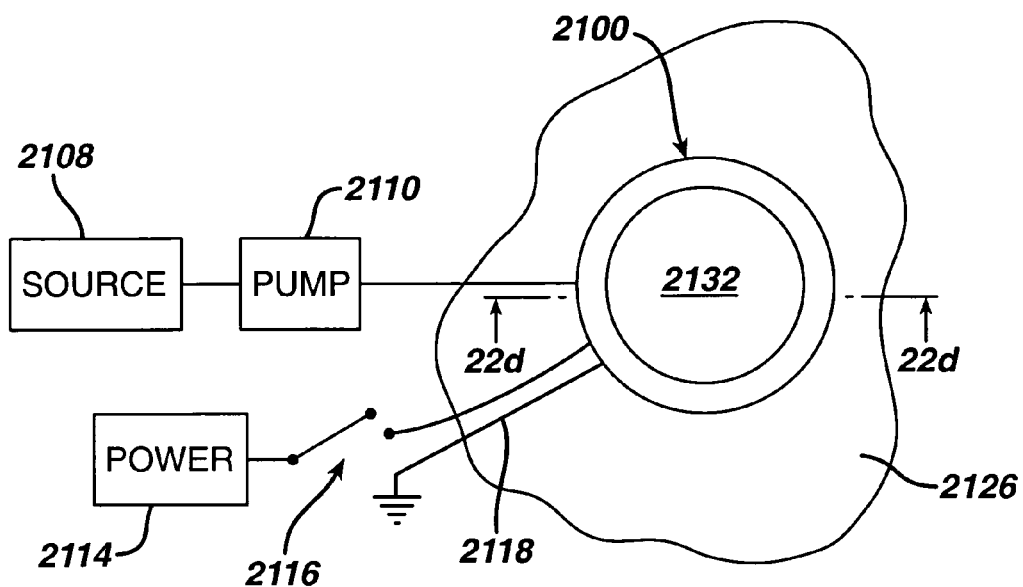
FIG. 22c illustrates the soft tissue retractor expanded in the incision and activated in the expanded position.
Figure 22D:
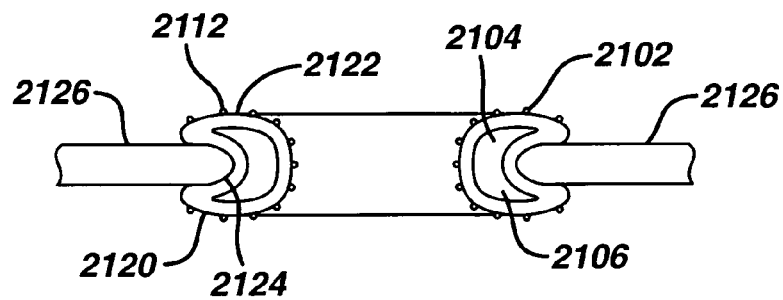
FIG. 22d illustrates a sectional view of the soft tissue retractor of FIG. 22c as taken along line 22d-22d therein.

When expanded, as shown in FIGS. 22c and 22d, the flexible bladder 2102 is preferably in the shape of a grommet and has intra and extracorpeal rings 2120, 2122 that define a channel 2124 in which tissue 2126 is disposed. Referring now to FIGS. 22a, 22b, 22c, and 22d, the operation of the soft tissue retractor will now be described. As shown in FIG. 22a, an incision 2128 is made in the tissue 2128 and if necessary a mechanical retractor 2130 is used to open the incision 2128 such that the soft tissue retractor 2100 can be placed in the incision 2128, as shown in FIG. 22b, while the rheological material 2106 is inactivated and the cavity 2104 is preferably substantially devoid of the same. Alternatively, the soft tissue retractor 2100 can be manually placed in the incision 2128 without the need for other instrumentation.

Referring now to FIGS. 22c and 22d, the rheological material is then delivered from the source 2108 by the delivery means 2110 to expand the flexible bladder 2102 to a desired shape, preferably circular. Where the rheological material is a MR fluid, the same is activated by closing the switch 2116 and thus powering the conductive coils 2112. This in turn generates a magnetic field in the cavity 2104. As discussed above, the flexible bladder 2102 is shaped such that the ends of the tissue, which define the incision, are captured in the channel 2124. The soft tissue retractor 2100 thereby defines an opening 2132 for accessing a body cavity with instrumentation in a less invasive manner.

Alternatively, the source 2108 and delivery means 2110 may be eliminated. In the alternative configuration, the rheological material is sealed in the cavity 2104. In the inactivated state, the retractor 2100 is placed in the incision 2128 and the retractor 2100 is manually manipulated into an open configuration, after which, the rheological material is activated to locked the retractor 2100 in the open position.

Referring now to FIGS. 23, 24a, 24b, 25a, and 25b, there are shown endoscopic instruments having means for locking and/or restricting the movement of end-effectors, such as jaws. Although, FIGS. 23, 24a, 24b, 25a, and 25b illustrate the means for locking and/or restricting the movement of end-effectors with respect to endoscopic instruments and grasper jaws, the same are given by way of example only and not to limit the scope or spirit of the present invention.

Figure 23:
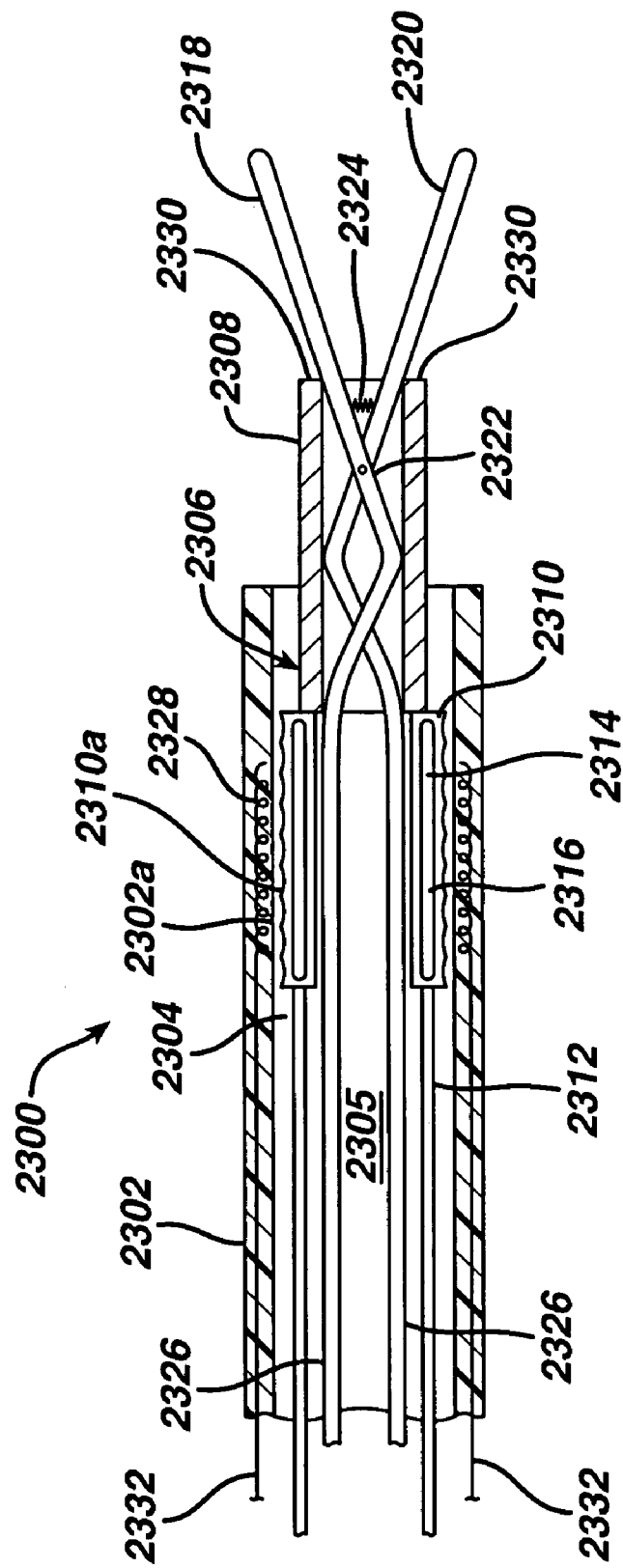
FIG. 23 illustrates a partial sectional view of an endoscopic instrument having a means for locking an end-effector in a desired position.

Referring specifically to FIG. 23, there is shown an endscopic instrument, generally referred to by reference numeral 2300, having an outer shaft 2302 that defines an outer lumen 2304. Inside the outer lumen 2304 there is slidingly disposed an inner shaft 2306 defining an inner lumen 2305. The inner shaft 2306 comprises a rigid distal tube 2308, a flexible cylindrical bladder 2310, and a proximal tube 2312. The bladder 2310 defines a cavity 2314 which has a rheological material 2316 disposed therein, preferably a MR fluid. The instrument 2300 further comprises first and second jaws 2318, 2320 that can be articulated between open and closed positions in any manner known in the art. Preferably, the first and second jaws 2318, 2310 are rotatably pinned at joint 2322 and biased in an open position by spring 2324. Control rods 2326 are connected to a proximal handle (not shown). Further provided is a means for activation of the MR fluid, which is preferably an electromagnet. The electromagnet comprises a coiled conductor 2328 disposed in or around the outer shaft 2302 proximate the bladder 2310.

In operation, a user manipulates the instrument to open and close the first and second jaws 2318, 2320 to a desired position, preferably by either withdrawing or extending the inner shaft 2306 relative to the outer shaft 2302. This results in the first and second jaws acting against surface 2330 of the rigid distal tube 2308 to open and close the same. When the first and second jaws 2318, 2320 are in a desired position the coiled conductor 2328 is supplied current through leads 2332 to energize the same, create a magnetic field and thus, activate the MR fluid to a desired state, preferably to a near solid state. An outer surface 2310a of the bladder 2310 has a means for preventing movement of the inner shaft 2306 relative to the outer shaft 2302 when the MR fluid is activated. Preferably, the outer surface 2310a has at least one locking projection and an inner surface 2302a of the outer shaft 2302 has a corresponding locking groove (or vice versa). When not activated, the projections are not rigid and cannot engage the corresponding locking grooves. However, when activated, the projections are sufficiently rigid to engage the corresponding locking grooves to prevent any relative movement between the inner and outer 2306, 2302 shafts. Alternatively, a frictional surface can be provided on the outer 2310a and/or inner 2302a surfaces to prevent or reduce the relative movement between the inner and outer 2306, 2302 shafts when the MR fluid is activated.

Those skilled in the art will appreciate that the instrument 2300 disclosed in FIG. 23 can be made to lock in any position, whereas such instruments of the prior art lock in only a fully closed position. Furthermore, while shown as a grasper (tissue forces are applied while closing the jaws), the instrument 23 can also be configured as a dissector (tissue forces are applied while closing the jaws). Further, if the jaws are configured for electrosurgery, and in particular for bipolar electrosurgery, the jaws can be prevented from fully closing to prevent shorting of the electrically conductive jaws with each other.

Figure 24A:
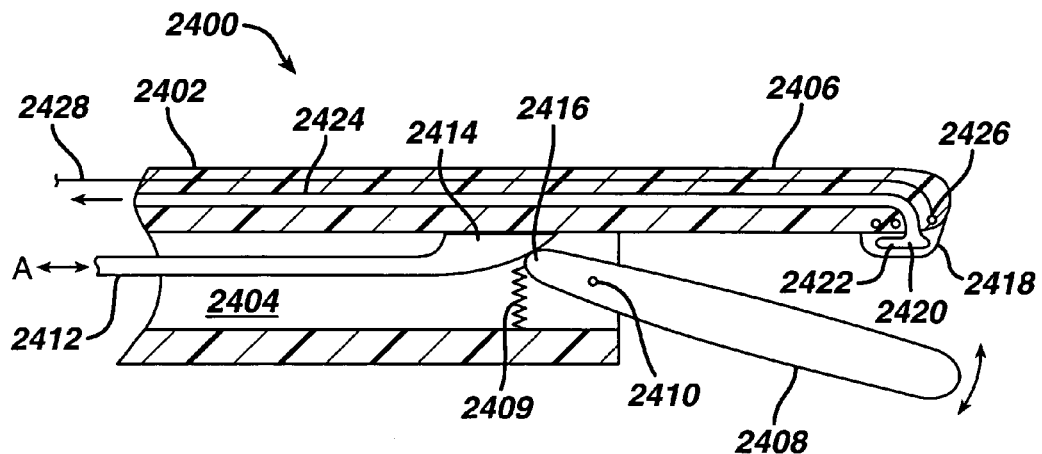
FIGS. 24a and 24b illustrate partial sectional views of an endoscopic instrument having means for preventing jaws of an end-effector from fully closing, where
Figure 24B:
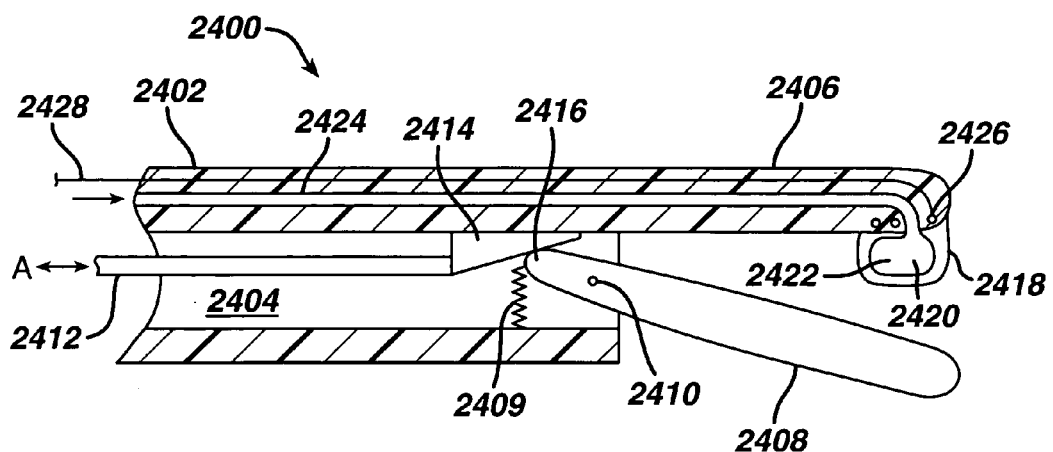

Referring now specifically to FIGS. 24a and 24b, there is shown an endoscopic instrument, generally referred to by reference numeral 2400. Instrument 2400 comprises an outer shaft 2402 defining a lumen 2404. The instrument 2400 further comprises first and second jaws 2406, 2408. Preferably, the first jaw 2406 is fixed and is integrally formed with a distal end of the outer shaft 2402 while the second jaw 2408 is pivotably disposed on the distal end of the outer shaft 2402 at a pinned joint 2410. A means is provided for articulating the first and/or second jaws 2406, 2408 between open and closed positions. Preferably, such means includes biasing the second jaw 2408 in a open position with a spring 2409 and a control rod 2412 having a wedge 2414 at an end thereof which engages a free end 2416 of the second jaw 2408. Manipulation of the control rod in direction A causes the second jaw 2408 to open and close relative to the first jaw 2406.

The instrument 2400 further comprises a flexible bladder 2418 defining a cavity 2420 in which a rheological material 2422 is disposed. A conduit 2424 is provided in the outer shaft 2402 which is in fluid communication at one end with a pumping and storage means, such as a syringe or squeeze bulb (not shown) and at another end with the cavity 2420. When no or a negligible amount of rheological material, such as an MR fluid is in the bladder, the second jaw 2408 is not restrained from fully closing against the first jaw 2406, particularly if the bladder 2418 is recessed in the first jaw 2406. However, when the MR fluid is pumped from a source into the cavity 2420 and activated by applying current to conductive coils 2426 through leads 2428 the bladder 2418 expands and becomes rigid as is shown in FIG. 24b. When expanded and rigid, the bladder 2418 prevents the first and second jaws 2406, 2408 from fully closing. Although rheological fluids are preferred because of their ability to become rigid, any fluid can be disposed in the bladder 2418 to prevent the first and second jaws 2406, 2408 from closing, particularly if the bladder material is thick and tough.

Figure 25A:
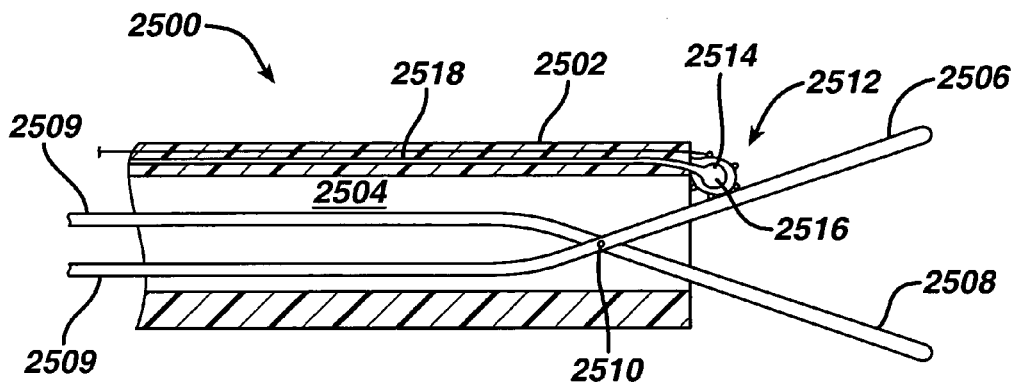
FIGS. 25a and 25b illustrate partial sectional views of an endoscopic instrument having means for preventing jaws of an end-effector from fully opening, where
Figure 25B:
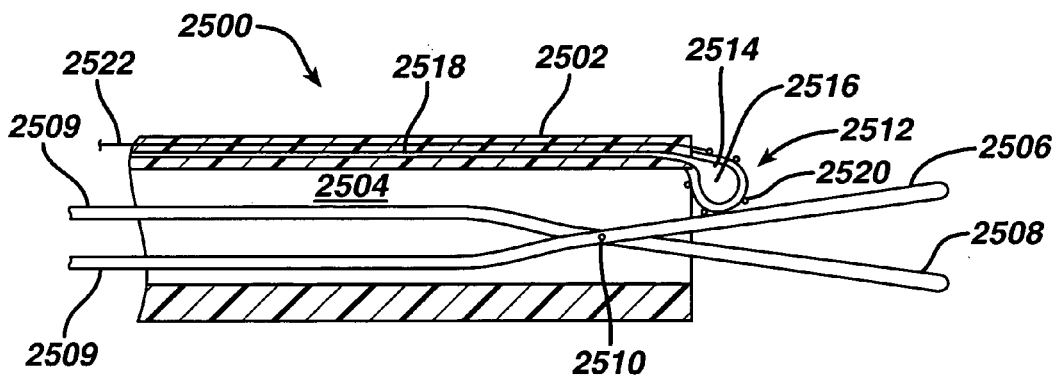

Referring specifically now to FIGS. 25a and 25b, there is shown an endoscopic instrument, generally referred to by reference numeral 2500. Instrument 2500 comprises an outer shaft 2502 defining a lumen 2504. The instrument 2500 further comprises first and second jaws 2506, 2508. Preferably, the first and second jaws 2506, 2508 are pivotably disposed on the distal end of the outer shaft 2502 at a pinned joint 2510. A means is provided for articulating the first and/or second jaws 2506, 2508 between open and closed positions as is known in the art. Preferably, the means is provided by manipulation of one or more control rods 2509 disposed in the lumen 2504.

The instrument 2500 further comprises a flexible bladder 2512 disposed at a distal end of the outer shaft 2502 and corresponding to at least one of the first and second jaws 2506, 2508. The bladder 2512 defines a cavity 2514 in which a rheological material 2516 is disposed. A conduit 2518 is provided in the outer shaft 2502 which is in fluid communication at one end with a pumping and storage means, such as a syringe or squeeze bulb (not shown) and at another end with the cavity 2514. When no or a negligible amount of rheological material, such as an MR fluid is in the bladder 2512, the first and second jaws 2506, 2508 are not restrained from fully opening. However, when the MR fluid is pumped from a source into the cavity 2514 and activated by applying current to conductive coils 2520 through leads 2522 the bladder 2512 expands and becomes rigid as is shown in FIG. 25b. When expanded and rigid, the bladder 2512 prevents the first and second jaws 2506, 2508 from fully opening.

Figure 26C:
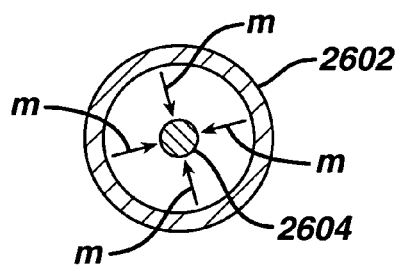
FIG. 26c illustrates a sectional view of the conformable shaft as taken along line 26c-26c of FIG. 26b.

Referring now to FIGS. 26a, 26b, and 26c, there is shown a conformable shaft, generally referred to by reference numeral 2600. The conformable shaft 2600 has an outer shaft 2602, an inner shaft 2604, and a distal end plate 2606. At a proximal end, a magnet 2608 is slidingly disposed in a cavity 2610 defined by the inner and outer shafts 2604, 2602. The magnet 2608 is connected to a pull 2612 for facilitating the sliding of the magnet 2608. A portion of the inner shaft 2614 at the proximal end of the inner shaft 2604 is composed of a low magnetic permeability material, such as plastic, or titanium. The remainder of the inner shaft 2604, as well as the outer shaft 2602, and the end plate 2606 are made of a flexible soft magnetic alloy, such as a very thin fully annealed steel with a high magnetic permeability. In a portion of the cavity 2610 not occupied by the magnet 2608, is disposed a rheological material, preferably an MR fluid 2616. A seal 2618 is provided to prevent the MR fluid from leaking into the portion of the cavity 2610 occupied by the magnet 2608. Alternatively, the MR fluid 2616 can be disposed in a sealed bag (not shown) that is disposed in the cavity 2610.

In FIG. 26a, the magnet is radially magnetized and is shielded by the low magnetic permeability material 2614 thereby opening a magnetic field circuit. As a result, no magnetic field is induced in the MR fluid and the MR fluid remains viscous. In the viscous state, the conformable shaft 260 can be manipulated into a desired shape. As shown in FIG. 26b, when the magnet 2608 is slid distally such that the low magnetic permeability material 2614 no longer shields the magnet, a magnetic field circuit is created. The magnetic field flux lines are designated by m. As shown in FIGS. 26b and 26c, the flux lines m travel from the outer shaft 2602, through the MR material, to the inner shaft 2604, and back to the magnet 2608. The magnet 2608 is preferably slid by depressing the pull 2612 in the direction of arrow A.

With the generation of the magnetic field through the MR fluid 2616, the MR fluid is activated and depending on the strength of the applied field, the conformable shaft 2600 becomes stiff. The conformable shaft 2600 can be made pliable by withdrawing the magnet 2608 into the position as shown in FIG. 26a.

Preferably, the conformable shaft 2600 is supplied with an end effector 2620 at the distal and/or proximal ends thereof. The end effector can be a forceps, electrode, clamp, or the like. As discussed above with regard to FIGS. 7a, 7b, 8a, 8b, 8c, 8d, the end effector can itself have a flexible bladder, which defines a cavity, and has a rheological material disposed therein. Additionally, the end-effector can utilize a mono or bipolar electrode arrangement, in which case the leads can be supplied to the end-effector via a hollow inner shaft 2604. Furthermore, additional MR fluid can be directed into the end-effector to enlarge the same in which case the displacement of the magnet 2608 can be used to "pump" additional MR fluid from the cavity 2610 into the end-effector.

Although described by way of an MR fluid that is activated by a magnet 2608, ER fluids can also be used with a current carrying member to generate a current in the ER fluid.

Alternatively, a bundle of high permeability wires, such as steel can be used in place of the inner shaft 2604. The wires are more pliable than the inner shaft 2604 and can also provide a return route for the magnetic field circuit. As another alternative, the outer shaft 2602 can be an elastomer or plastic tube having extruded high magnetic permeability wires disposed in the wall thereof. The wires can run longitudinally along the length of the outer shaft 2602 or be braided along the longitudinal length. As yet another alternative, high magnetic permeability members can be disposed in the MR fluid 2616 suspension to aid in carrying the magnetic field through the MR fluid 2616. The high-magnetic permeability members can be shaped as spheres, cubes or other shapes, or as short fibers that are dispersed throughout the MR fluid 2616, in which case a means for agitating the MR fluid may be necessary. Alternatively, the high-magnetic permeability members may be continuously looped wires that are fixed at one or both of the distal and proximal ends and which may be used in addition to or in place of the inner shaft 2604.

Figure 27B:
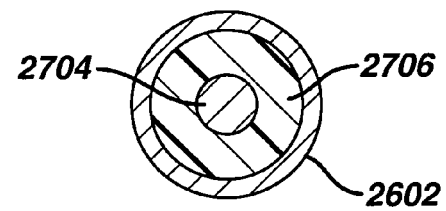
Figure 27A:
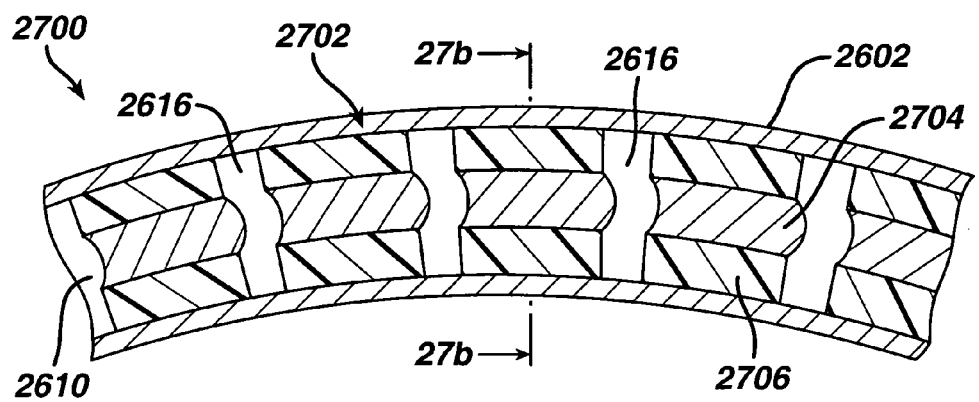

Referring now to FIGS. 27a and 27b there is shown an alternative configuration to the conformable shaft 2600 of FIG. 26a, generally referred to by reference numeral 2700. In FIG. 27a, the distal and proximal ends are assumed to be similarly configured, that is with a distal plate and/or end effector and a slidable magnet having a shielded (inactivated) and unshielded (activated) position. In the conformable shaft 2700 of FIG. 27a, a plurality of shaft segments 2702 are disposed in the cavity 2610 of the outer shaft 2602 along with MR fluid 2616. The shaft segments are comprised of a high permeability material core 2704 and a low permeability outer covering 2706. The shaft segments 2702 have an outer diameter such that they fit snugly within the cavity 2610 and are shaped at their ends such that they can interact with each other, such as having a concave proximal end and a convex distal end. As the magnet 2608 is moved into the unshielded position (as shown in FIG. 26b), a magnetic field is created through the outer shaft 2602, into the inner cores 2704 of the shaft segments 2702, through the MR fluid 2616, and back to the magnet 2608 thereby activating the MR fluid into a rigid state. In this state, the conformable shaft 2700 is made rigid.

Figure 28B:
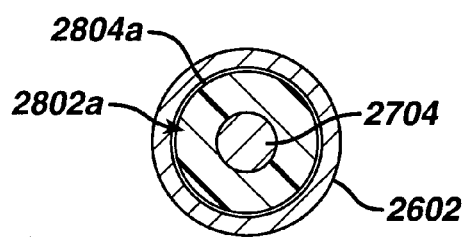
Figure 28C:
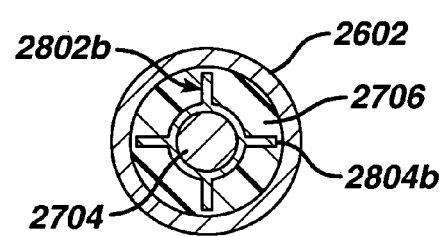
Figure 28A:
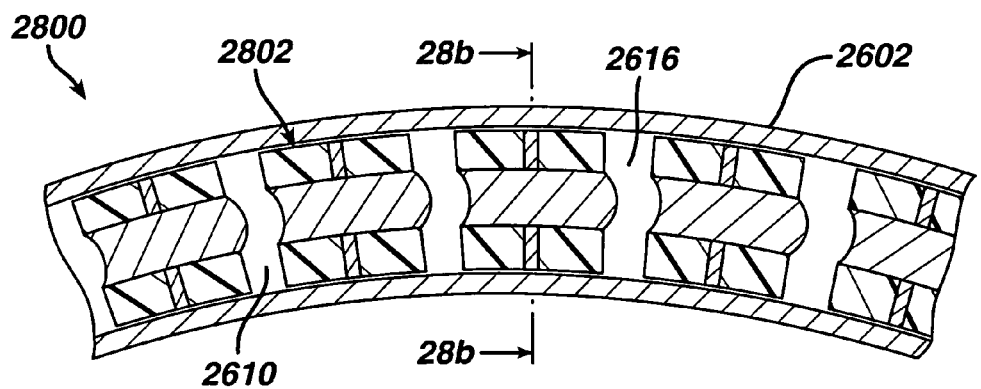

Referring now to FIGS. 28a, 28b, and 28c, there is shown an alternative to the conformable shaft of FIG. 27a, the conformable shaft of FIG. 28a being generally referred to by reference numeral 2800. As shown in FIGS. 28b and 28c, the shaft segments 2702 further have a protruding member 2802 which is a solid disc 2802a in the configuration of FIG. 28b and a fingered disk 2802b in FIG. 28c. The disks 2802a, 2802b are sized such that a small amount of MR fluid is disposed between the ends 2804a, 2804b of the disks 2802a, 2802b and the inner wall of the outer shaft 2602. Upon activation of the MR fluid (displacement of the magnet 2608 into the unshielded position shown in FIG. 26b) a very high localized magnetic field will be produced between the disk ends 2804a, 2804b and the inner wall of the outer shaft 2602, thereby producing a very rigid portion of MR fluid and providing a resistance to bending of the shaft 2800.

Figure 29A:
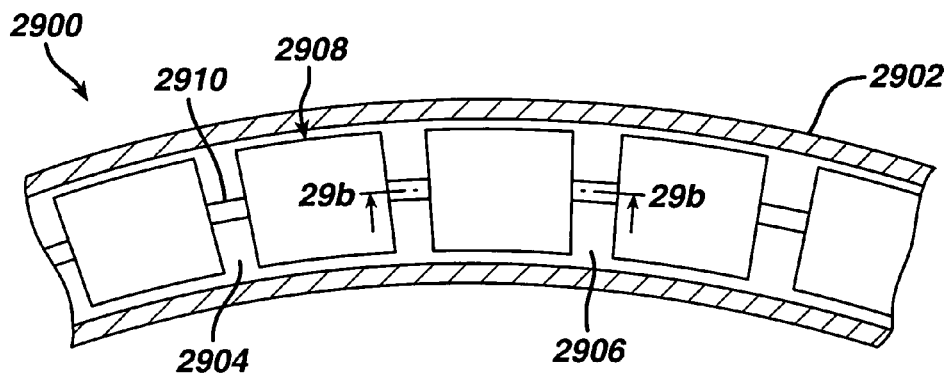
FIG. 29a illustrates a partial sectional view of a conformable shaft.
Figure 29B:
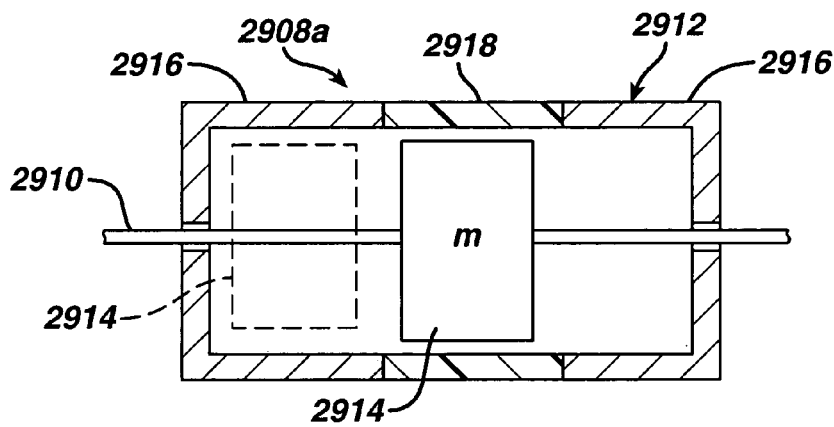
Figure 29C:
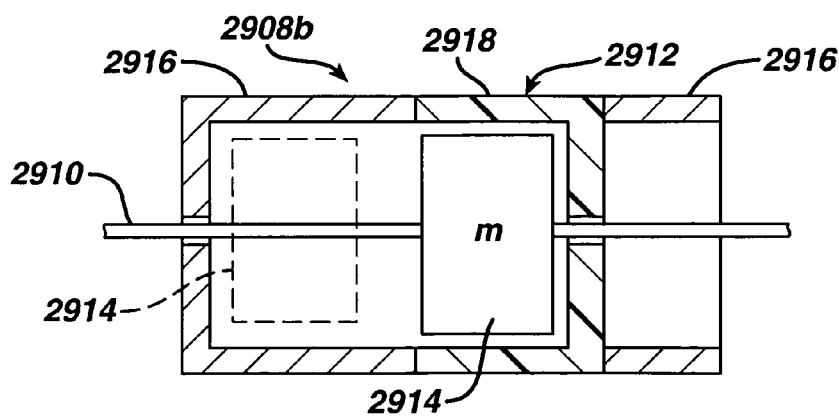

Referring now to FIGS. 29a, 29b, and 29c, there is illustrated yet another configuration of a conformable shaft, generally referred to by reference numeral 2900. Conformable shaft 2900 has an outer shaft 2902 of a high magnetic permeability material, such as a fully annealed steel. The outer shaft 2902 defines a cavity 2904. In the cavity 2904 is disposed a rheological material, such as an MR fluid 2906 and a plurality of shaft segments 2908. The shaft segments are linked together by a cable 2910.

FIGS. 29b and 29c illustrate two versions of the shaft segments 2908. Each shaft segment 2908a, 2908b has an outer shell 2912 which houses a slidable magnet 2914. The shell 2912 is made of a portion 2916 having a high magnetic permeability and a portion 2918 having a low magnetic permeability. The magnets 2914 are connected to the cable 2910 and can be slid together back and forth between shielded (inactivated) positions shown in solid lines and unshielded (activated) positions shown by dotted lines. The cable 2910 is disposed through a corresponding hole in each end of the shaft segment 2908 which can be provided with a seal, if necessary to prevent MR fluid from entering the interior of the shell 2912.

In the shielded position, the magnets 2914 do not generate a magnetic field and thus do not activate the MR fluid 2906 in the cavity 2904 thereby providing for a conformable and pliable shaft. In the unshielded position, a magnetic field is generated by each magnet 2914 in the MR fluid 2906 thus activating the same and the shaft 2900 into a rigid state. The configuration of the conformable shaft 2900 where a plurality of activation magnets 2914 are utilized is particularly suited for shafts having a relatively long length where the magnetic field from a single activation magnet may not traverse the entire length of the shaft.

Referring now to FIG. 30 there is shown a portion of yet another conformable shaft, generally referred to by reference numeral 3000. Conformable shaft 3000 preferably includes a proximal end similar to that illustrated in FIG. 26a for activation and inactivation of the rheological material. Furthermore, conformable shaft has a distal end similar to that illustrated and described with regard to FIG. 26a, including all possible end effectors discussed above.

The conformable shaft 3000 has an outer shaft 3002 which defines a lumen 3004. The outer shaft is preferably configured similarly to that discussed above with regard to FIG. 26a, that is, it is thin and flexible and preferably composed of a high magnetic permeability material, such as a fully annealed steel. A rheological material 3006, such as an MR fluid is disposed in the lumen 3004. Further disposed in the lumen is a plurality of disks 3008. Each disk having a plurality of holes 3010 for acceptance of a plurality of wire fibers 3012 therein (only one of which is shown for clarity). The wire fibers 3012 are also preferably flexible and composed of a high magnetic permeability material, as are the disks 3008. The wire fibers 3012 are sized such that they fit loosely in their respective holes 3010 such that an annular gap exists between the outer surfaces of the wire fiber 3012 and the inner surfaces of the hole 3010. The gap is sufficiently sized such that the MR fluid 3006 disposed in the cavity 3004 can at least partially fill the gap.

Upon moving the magnet to an unshielded (activation) position, a magnetic field is generated through the outer shaft 3002, through the disks 3008, through the MR fluid (in the gaps between the holes 3010 and wire fibers 3012), and through the fibers 3012 which completes the magnetic circuit back to the magnet. As a result, the MR fluid in the gaps is activated thereby locking the fibers 3012 to the disks 3008. This has the effect of making the conformable shaft 3000 rigid.

Figure 31A:
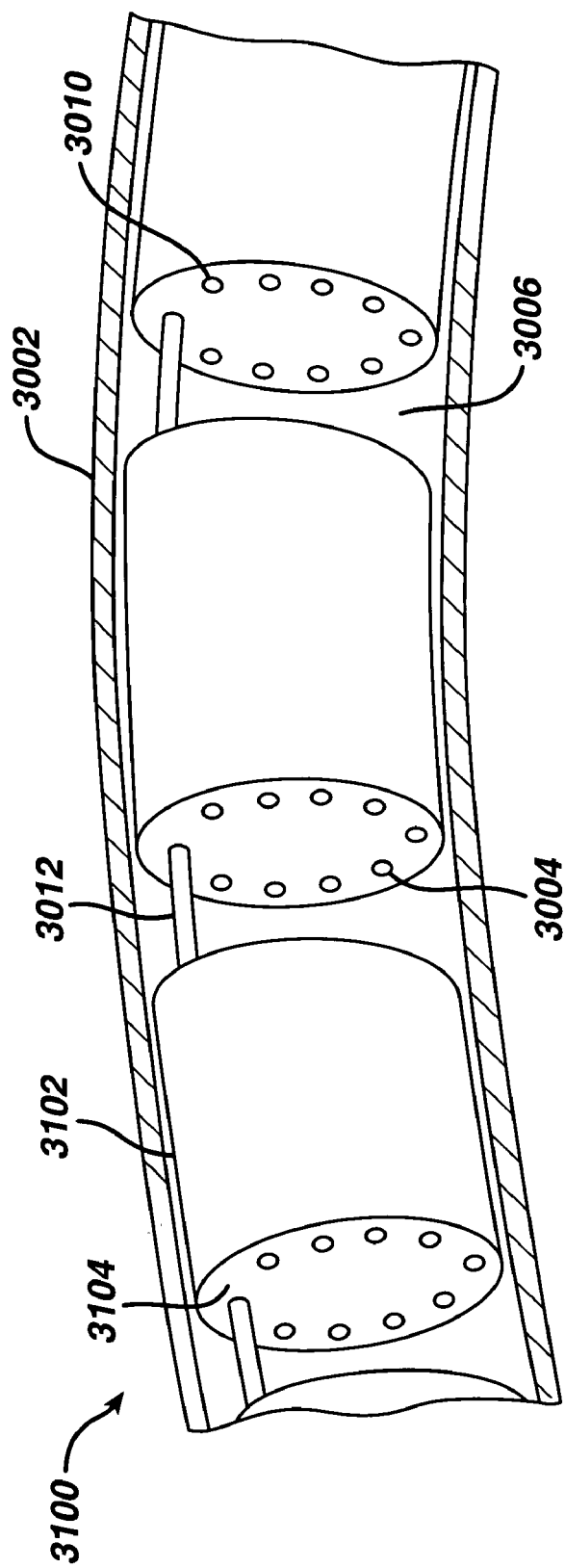
FIG. 31a illustrates an alternative version of the conformable shaft of FIG. 30.
Figure 31B:
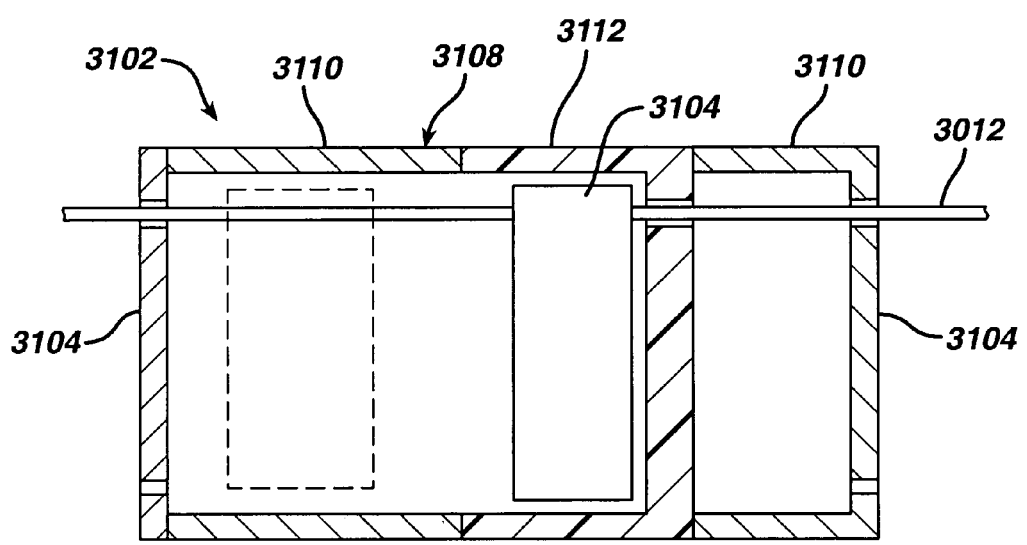

Referring now to FIGS. 31a and 31b, an alternative version of the conformable shaft is illustrated, the alternative version being generally referred to by reference numeral 3100. In the alternative version, the plurality of disks are replaced with shaft segments 3102. The shaft segments 3102 are similar in construction to that illustrated in FIG. 29c, however, each shaft segment includes disks 3104 on the ends thereof. The disks 3104 have a plurality of holes 3010 which house the wire fibers 3012 in the same manner as described above with regard to FIG. 30. However, where longer shaft lengths are necessary, each shaft segment 3102 comprises an activation magnet 3106 that is slidable in a shell 3108 between shielded (shown solid) and unshielded (shown dotted) positions. As discussed above with regard to FIG. 29c, the shell 3108 has a portion 3110 of high magnetic permeability material and a portion 3112 of low magnetic permeability material. When the magnet is disposed in the shielded position, the portion of low magnetic permeability material 3112 prevents a magnetic filed from being generated in the MR fluid 3006 disposed in the gaps between the wire fiber 3012 and holes 3010. However, when the magnets 3104 is slid to the unshielded (activation) position, the MR fluid in the gaps is activated as discussed above with regard to FIG. 30. Preferably, the magnets 3104 are all commonly slid in the shielded and unshielded positions by pulling the fibers 3012 in a corresponding direction. Alternatively, a dedicated wire (not shown) can be used for the same purpose.

Also provided is a heart valve repair/replacement ring. The ring (not shown) contains a rheological material, such as a MR fluid and a means for delivering the rheological material to the ring to expand the same. A pacing device responds to physiologic conditions and signals for the radial expansion of the valve annulus during exercise and/or physical exertion.

Still yet provided is a bone-lengthening scaffold (not shown). The scaffold has an internal plate and pin device having a rheological material to slowly expand or correct a bone injury or abnormality. A magnet can be applied to the internal device from the skin to activate the rheological material and slowly configure the bone into the desired shape.

While the devices described above have been specifically explained mainly with regard to MR and ER fluids, it is to be understood that fluid evacuation rheological materials may also be possible. Where applicable, it is to be understood by those in the art that the use of fluid evacuation rheological material generally require means for removing the fluid from the cavity for activation and returning the same to the cavity for inactivation. These means typically include a vacuum source, a pumping means, at least one valve, and appropriate tubing.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An impression device for making an impression of a desired feature, the impression device comprising:
   a flexible bladder bite bag having a cavity formed therein, the flexible bladder being conformable to a feature in a person's mouth as the desired feature;
   a magneto-rheological material disposed in the cavity of the flexible bladder; and
   a magnet for generating a magnetic field in at least a portion of the magneto-rheological fluid and capturing an impression of the desired feature thereby, wherein the magnet further comprises a u-shaped magnet having first and second ends adapted to be disposed between teeth in the person's mouth and an inner surface of a cheek.

2. The impression device of claim 1, wherein the flexible bladder further comprises a pocket corresponding to each of the first and second ends of the magnet for retaining the same therein.

* * * * *